US009260535B2

(12) United States Patent
Albers et al.

(10) Patent No.: US 9,260,535 B2
(45) Date of Patent: Feb. 16, 2016

(54) POLYSACCHARIDE SUITABLE TO MODULATE IMMUNE RESPONSE

(75) Inventors: Ruud Albers, Rockanje (NL); Jari Helin, Helsinki (FI); Werner Klaffke, Vlaardingen (NL); Jean Hypolites Koek, Vlaardingen (NL); Petronella Anna Kreijveld, Vlaardingen (NL); Jari Natunen, Helsinki (FI); Erwin Werner Tareilus, Vlaardingen (NL); Richardus Paulus Anton Oranje, Vlaardingen (NL)

(73) Assignee: NutriLeads B.V., Rockanje (NL)

( * ) Notice: Subject to any disclaimer, the term of this patent is extended or adjusted under 35 U.S.C. 154(b) by 100 days.

(21) Appl. No.: 13/514,937

(22) PCT Filed: Nov. 16, 2010

(86) PCT No.: PCT/EP2010/067528
§ 371 (c)(1),
(2), (4) Date: Nov. 19, 2012

(87) PCT Pub. No.: WO2011/069781
PCT Pub. Date: Jun. 16, 2011

(65) Prior Publication Data
US 2013/0064858 A1 Mar. 14, 2013

(30) Foreign Application Priority Data

Dec. 11, 2009 (EP) ..................................... 09178876

(51) Int. Cl.
*A61K 31/715* (2006.01)
*C08B 37/00* (2006.01)

(52) U.S. Cl.
CPC .......... *C08B 37/0045* (2013.01); *C08B 37/0048* (2013.01)

(58) Field of Classification Search
CPC ............. C08B 37/0048; C08B 37/0045; C08B 37/006; C08B 37/0003
USPC ........................................ 514/54; 536/123.1
See application file for complete search history.

(56) References Cited

U.S. PATENT DOCUMENTS

| 6,794,495 B1* | 9/2004 | Sorensen .................... 530/395 |
| 2003/0159178 A1 | 8/2003 | Ulvskov et al. |
| 2004/0241299 A1* | 12/2004 | Zhang ............................ 426/435 |
| 2005/0002962 A1 | 1/2005 | Pasco et al. |
| 2005/0129789 A1* | 6/2005 | Shirota ......................... 424/765 |

FOREIGN PATENT DOCUMENTS

| EP | 1 550 448 A1 | 7/2005 |
| JP | 7109226 A * | 4/1995 |
| WO | WO-01/76609 A1 | 10/2001 |
| WO | WO-2007/109802 A2 | 9/2007 |
| WO | WO-2009/071425 A1 | 6/2009 |
| WO | WO-2009/080447 A1 | 7/2009 |

OTHER PUBLICATIONS

Bauer et al. (Wiener medizinische Wochenschrift (1946), (1999) vol. 149, No. 8-10, pp. 185-189)(Abstract sent).*
Murai et al.; JP 7109226 A; Apr. 25, 1995 (Machine-English Translation).*
Hansen, Karin M. et al. "Enzyme Assay for Identification of Pectin and Pectin Derivatives. Based on Recombinant Pectate Lyase", Journal of AOAC International, vol. 84. No. 6, Mar. 14, 2000, pp. 1851-1854, XP-002581495.
International Search Report for PCT/EP2010/067528—mailed Dec. 20, 2010.
Lau, James M. et al. "Structure of the backbone of rhamnogalacturonan I, A pectic polysaccharide in the primary cell walls of plants", Carbohydrate Research, vol. 137, May 14, 1984, pp. 111-125, XP-002581494.
Nakamura, Akihiro et al. "Analysis of Structural Components and Molecular Construction of Soybean Soluble Polysaccharides by Stepwise Enzymatic Degradation", Bioscience, Biotechnologie,Biochemistry, vol. 65, No. 10, Apr. 6-Jun. 8, 2001, pp. 2249-2258, XP-002581998.
Nergard, Cecilie Sogn et al. "Structural and immunological studies of a pectin and a pectic arabinogalactan from Vernonia kotschyana Sch. Bip. ex Walp. (Asteracae)", Carbohydrate Research, vol. 340, Dec. 8, 2004, pp. 115-130, XP-002581996.
Oechslin, Rahel et al. "Pectic substances isolated from apple cellulosic residue: structural characterisation of a new type of rhamnogalacturonan I", Carbohydrate Polymers, vol. 51, May 22-Jun. 13, 2002, pp. 301-310, XP-002582034.
Zhao, Zhihui et al. "Structures and immunological activities of two pectic polysaccharides from the fruits of Ziziphus jujuba Mill. cv. jinsixiaozoa Hort.", Food Research International. Jan. 5-May 22, 2006, pp. 917-923, XP-002581997.
Sakurai, et al. "B-cell proliferation activity of pectic polysaccharide from a medicinal herb, the roots of *Bupleurum falcatum* L. and its structural requirement", Immunology, 1999, vol. 97, pp. 540-547.
Westereng, et al. "Release and characterization of single side chains of white cabbage pectin and their complement-fixing activity", Mol. Nutr. Food Res., 2009, vol. 53, pp. 780-789.

* cited by examiner

*Primary Examiner* — Shaojia Anna Jiang
*Assistant Examiner* — Michael C Henry
(74) *Attorney, Agent, or Firm* — Sunit Talapatra; Foley & Lardner LLP

(57) ABSTRACT

Objective of the present invention is to provide polysaccharides which modulate immune response, and which can be used as ingredients in edible products or pharmaceutical compositions. The present invention provides such polysaccharides obtained from the species *Camellia sinensis*, which comprise a rhamnogalacturonan-I core, and wherein the molar ratio of galacturonyl acid residues to rhamnosyl residues in the backbone of the polysaccharide is close to 1:1. The present invention also provides edible products or pharmaceutical compositions containing such polysaccharides, in order to modulate immune response.

6 Claims, 3 Drawing Sheets

POLYSACCHARIDE SUITABLE TO MODULATE IMMUNE RESPONSE

CROSS-REFERENCE TO RELATED APPLICATIONS

This application is a National Stage application of PCT/EP2010/067528, filed Nov. 16, 2010, which claims priority from European Application No. 09178876.0, filed Dec. 11, 2009. These applications are herein incorporated by reference in their entirety.

The present invention relates to a polysaccharide that can be used to modulate immune response. The invention further relates to the polysaccharide for use as a medicament. The present invention also relates to an edible product or a pharmaceutical composition comprising the polysaccharide. The invention also relates to a method for preparation of an edible product or pharmaceutical composition comprising the polysaccharide. The invention further relates to a method for isolation of the polysaccharide.

Many adults in the western world suffer two to five colds a year, and infants and pre-school children even have an average of four to eight colds a year. The upper respiratory tract infections, like common colds and flu, are together with gastro-intestinal infections the most important reasons of absenteeism at work or school. In a lifetime of 75 years, we suffer on average from over 200 episodes of common cold. This means that if each cold lasts for five to seven days we spend around three years of our life coughing and sneezing with colds. The need and interest of a consumer in 'self prevention' and 'self treatment' of these acute infections are therefore high.

A recent interest in the field of functional food ingredients is the use of immunomodulators for enhancing host defence responses, for instance, to provide more protection against the common cold. An important part of the host defence response is the innate immune system. The innate arm of the immune system is a rapidly activated first line of defence against pathogens. It involves amongst others phagocytic and natural killer (NK) cells. Phagocytic cells such as neutrophils, monocytes and macrophages can generate reactive oxygen species (ROS) to kill pathogens such as fungi, bacteria and virus-infected cells. NK cells can kill target cells that have lost or express insufficient amounts of MHC class I, a frequent event in tumor- or virus-infected cells.

Some edible products or food products have been reported to have immunostimulating properties. For example, US 2005/0002962 A1 discloses a melanin preparation of botanicals such as Echinacea, American ginseng, black walnut, green tea, Parthenium integrifolium, Korean ginseng, alfalfa sprouts, ginger, goldenseal, red clover, dandelion, black cohosh, licorice, chamomile, milk thistle, alfalfa, horsetail, *astragalus*, gotu kola, feverfew, valerian, hawthorn, rosemary, saw palmetto, ephedra, pau d'arco, ginkgo, garlic, St. John's wort, *Agaricus bisporus* (common mushroom), *Agaricus bisporus* brown strain (portabella mushroom), *Lentinus edodes* (shiitake mushroom) or *Boletus edulis* (porcini mushroom) as an immune stimulatory composition.

WO 2009/071425 A1 and WO 2009/080447 A1 disclose the immunostimulating effects of fractions including substantial amounts of oligosaccharides and/or low molecular weight from plants of the Asclepiadoideae subfamily (such as *hoodia*) and the Alliaceae family (such as onion and garlic from the *Allium* genus), respectively.

Westereng et al. (Mol. Nutr. Food Res. 2009, vol. 53, p. 780-789) describe release and characterization of single side chains of pectic material extracted from white cabbage (*Brassica oleracea* var. *Capitata, Bartolo* cultivar) and their complement-fixing activity (which plays a role in the human immune system). Westereng et al. focus on the side chains as the elements of the pectic material being active in complement fixing, and the authors indicate that structural elements containing multiple side chains are necessary for efficient complement-fixing activity. The pectic material contained two fractions, having a molecular weight of 630 and 40 kDa, respectively, and was active in complement fixing. The average ratio between galacturonyl acid and rhamnosyl residues of the polysaccharides was 5.7. The pectic material was degraded by beta-elimination into a charged fraction and two neutral fractions, having molecular weights of 90, 17, and 8 kDa, respectively. The neutral fractions consist of side chains released by beta-elimination, and the fraction of 17 kDa showed complement fixing activity, while the 8 kDa fraction did not show complement fixing activity; the 90 kDa fraction was not tested. Apparently, based on molecular weight, the large neutral fraction contains molecules having at least two side chains, while the small neutral fraction contains only single side chains.

Sakurai et al (Immunology, 1999, vol. 97, p. 540-547) disclose a pectic polysaccharide fraction (called bupleuran 2IIc) that was prepared from a medicinal herb (*Bupleurum falcatum* L.) and administered orally to mice. The polysaccharide comprises a galacturonic region and a rhamnogalacturonan core rich in neutral sugar chains, and it is suggested that the side chains of the RG core are important for the mitogenic activity of the polysaccharide.

WO 2001/76609 A1 discloses the use of polygalacturonic acids as ingredients in food. The polygalacturonic acids are prepared by endopolygalacturonidase treatment of plants contain pectin. The polygalacturonic acids are useful as viscosifier in food products. The pectins are known to have a useful physiological effect.

U.S. Pat. No. 6,794,495 discloses a composition of extensin and pectin, enhancing the immune system. Extensin is hydroxyproline-rich glycoprotein abundant in the cell walls of dicotyledons.

Lau et al. (Carbohydrate Research, 1985, vol. 137, p. 111-125) disclose an RG-I polysaccharide, $M_W$ about 200 kDa, alternating sequence of Rha and GalA about 400 residues. Nature of side chains is still in question, although they contain L-arabinosyl and D-galactosyl residues.

US 2003/0159178 A1 discloses a rhamongalacturonan-I polysaccharide having a ratio of GalA/Rha ~1.3. The polysaccharides can be derived from genetically modified potato, wherein the modification of the plant has resulted into reduced amount of arabinose or galactose in the side chains of the RG-I.

EP 1 550 448 A1 discloses a histamine release inhibitor comprising a pectin.

Hansen et al. (Journal of AOAC International, 2001, vol. 84, p. 1851-1854) discloses a method for analysis of pectin.

Nergard et al. (Carbohydrate Research, 2005, vol. 340, p. 115-130) disclose polysaccharides from the plant *Vernonia kotschyana*, and their effect on complement fixing.

Zhao et al. (Food Research International, 2006, vol. 39, p. 917-923) disclose polysaccharides involved in immunological activity, although it is not specified which part of the polysaccharide is involved in modulation of immune response.

Nakamura et al. (Biosci. Biotechnol. Biochem., 2001, vol. 65, p. 2249-2258) disclose the structure of polysaccharides derived from soybean.

Oechslin et al. (Carbohydrate Polymers, 2003, vol. 51, p. 301-310) disclose the structure of RG-I isolated from apple cellulosic residue.

SUMMARY OF THE INVENTION

In spite of the disclosure of the prior art, there is a desire to increase the natural defence of the human body against intruders which may cause a cold or the flu, or any other symptom which causes the consumer to feel weak or ill. The consumer is especially interested to achieve this goal with naturally occurring compounds or ingredients, especially as part of a common food product or diet, as the consumer generally does not want to rely on medicaments only. In order to achieve this, the consumer may consume one or more ingredients or edible products that modulate the immune response of the consumer and provide the required natural defence. Hence there is a constant need for new or alternative edible products, especially food products having such immunostimulating properties. It is an objective of the present invention to provide such edible products, especially food products. Another objective of the present invention is to provide substances which can be used in such edible products or food products, especially substances which can be used to modulate the immune response of the person consuming such substance without having a negative influence on the edible product or food product itself.

In order to be a useful ingredient for an edible product or a food product, the properties of the ingredient should be such that the ingredient can be used in an edible product or a food product without negative influence on the properties of the edible product or food product. These properties may be related to the organoleptic properties of the ingredient, like taste, flavour, smell, colour. For example the ingredient should not have a bad taste or smell, otherwise consumers will not like the edible product and will not consume it. On the other hand, the property may also be related to some technical aspects of the ingredient when being used as an ingredient in an edible product. For the food manufacturer it is important that the ingredient does not negatively influence technical properties of the edible product or food product, such as texture, viscosity, homogeneity, emulsification, and other relevant properties.

Hence it is another objective of the present invention to provide an ingredient that can modulate immune response of a consumer upon consumption, and which does not negatively influence the properties of the edible product or food product. For instance it is an objective of the present invention to provide an ingredient which does not or only very limitedly leads to a thickening effect when used in the edible product or food product. It is another objective to provide an ingredient that can modulate the immune response of a consumer upon consumption of that ingredient and that has a technical function as an emulsifier or stabiliser, so that can be saved on the use of other emulsifiers or stabilisers.

One or more of these objectives have been met by a polysaccharide obtained from plants of the species *Camellia sinensis*, wherein the backbone of the polysaccharide comprises alternating rhamnogalacturonan-I cores and alpha(1,4)-linked polygalacturonic acid or alpha(1,4)-linked oligogalacturonic acid cores, wherein the molar ratio of galacturonyl acid residues to rhamnosyl residues in the backbone of the polysaccharide ranges from 2.5:1 to 1:1, and that has a molecular weight of at least 70 kDa. Hence the amount of alpha(1,4)-linked polygalacturonic acid and/or alpha(1,4)-linked oligogalacturonic acid cores in this polysaccharide is very low. The immuno-stimulation, immuno-suppression or immuno-modulation effects in the prior art are based on various molecular structures, including small alkaloid type molecules and glucan type polysaccharides or very heterologous combinations of these. Their effects differ in magnitude. The present invention provides well characterized isolated polysaccharide materials with well characterized activities.

The advantage of the polysaccharide according to the invention is that it is not only suitable to modulate immune response, and therewith increase the natural defence of a consumer against the cold or flu, or a similar condition, but it is also useful as an ingredient in edible products, more specifically food products. Compared to standard pectins, the thickening effect of the polysaccharide according to the invention is only very limited. This way the ingredient may be used in various food products, especially liquid food products such as beverages and soups, without negatively affecting the properties such as viscosity and texture of those food products. Additionally the use of the polysaccharide is not limited to food products, it may also be used as a medicament.

Accordingly in a first aspect the present invention provides a polysaccharide obtained from plants of the species *Camellia sinensis* wherein the backbone of the polysaccharide comprises alternating rhamnogalacturonan-I cores and alpha(1,4)-linked polygalacturonic acid or alpha(1,4)-linked oligogalacturonic acid cores, wherein the molar ratio of galacturonyl acid residues to rhamnosyl residues in the backbone of the polysaccharide ranges from 2.5:1 to 1:1, and wherein the polysaccharide has a molecular weight of at least 70 kDa. The first aspect of the invention also provides a preparation obtained from plants of the species *Camellia sinensis* comprising a polysaccharide according to the invention.

In a second aspect the present invention provides a polysaccharide according to the first aspect of the invention or a preparation obtained from plants of the species *Camellia sinensis* comprising a polysaccharide according to the first aspect of the invention for use as a medicament.

In a third aspect the present invention provides a polysaccharide according to the first aspect of the invention or a preparation obtained from plants of the species *Camellia sinensis* comprising a polysaccharide according to the first aspect of the invention for use as a medicament to modulate immune response, preferably in humans.

In a fourth aspect the present invention provides an edible product or pharmaceutical composition comprising a polysaccharide according to the first aspect of the invention or a preparation obtained from plants of the species *Camellia sinensis* comprising a polysaccharide according to the first aspect of the invention.

In a fifth aspect the present invention provides a method for preparation of an edible product or pharmaceutical composition comprising a polysaccharide according to the first aspect of the invention or a preparation obtained from plants of the species *Camellia sinensis* comprising a polysaccharide according to the first aspect of the invention, wherein the polysaccharide is brought into contact with at least one ingredient of the edible product or pharmaceutical composition.

Finally in a sixth aspect the present invention provides a method for isolation of a polysaccharide according to the first aspect of the invention or a preparation obtained from plants of the species *Camellia sinensis* comprising a polysaccharide according to the first aspect of the invention, comprising the step of preparing an aqueous extract of a suitable vegetable material, at a temperature between 20 and 100° C., during a period of between 1 and 6 hours, to release the polysaccharide of invention from the vegetable material; and subsequently purification of the extracted polysaccharide.

DETAILED DESCRIPTION

Unless defined otherwise, all technical and scientific terms used herein have the same meaning as commonly understood by one of ordinary skill in the art.

All percentages, unless otherwise stated, refer to the percentage by weight.

In case a range is given in the context of the present invention, the indicated range includes the mentioned endpoints.

Abbreviations: kDa-kilo Dalton; Gal-D-Galactose; GalA-D-Galacturonic acid; Rha-L-Rhamnose; Ara-L-Arabinose; Fuc-L-Fucose; Glc-D-Glucose; GlcA-D-Glucuronic acid. The L- and D-forms of these monomers as indicated here also apply to the monomers as indicated in the rest of this specification (which may not be abbreviated but written in full).

Vegetable material: in the context of the present invention a vegetable material refers to material from plant origin, and this material may origin from a vegetable or from a fruit (as commonly understood in kitchen or recipe context).

Preferred aspects disclosed in connection with either of the first, second, third, fourth, fifth and sixth aspects of the present invention may also be applicable to the other aspects of the present invention, mutatis mutandis. The various features and embodiments of the present invention, referred to in individual sections below apply, as appropriate, to other sections, mutatis mutandis. Consequently features specified in one section may be combined with features specified in other sections, as appropriate. All publications mentioned in this specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the claims.

Immune Response

By the term 'modulating immune response' as used herein, is meant that the activity or capacity of the immune system to defend the body is modulated. This may relate to immunostimulation or immuno-suppression. The primary task of the immune system is to protect against pathogens such as fungi, bacteria, viruses, protozoa and parasites. In this context, modulating immune response preferably means stimulation of the immune response. Suitably, stimulation of the immune response contributes to an enhanced natural defence of the human body. On the other hand, the immune system sometimes mounts an immune response against harmless substances, like house mite, dust or pollen, resulting in allergy. In addition, many physiological disorders, like hypercholesterolemia and obesity, result in a low-grade inflammatory status. Immune modulation in the context of abnormal immune responses, like allergy or inflammation, means dampening or counteracting the hypersensitivity immune response. The present invention not only relates to the primary task of the immune system, but also to this second 'abnormal' immune response.

Several assays can be used to identify components that could modify immunity. The present inventors chose the use of phagocytic and natural killer (NK) cells to aid the identification of immunostimulating compounds as these cells are part of the innate immune system, which is a rapidly activated non-specific first line of defence against pathogens.

Phagocytic cells such as neutrophils, monocytes and macrophages can generate reactive oxygen species (ROS) to kill pathogens such as fungi and bacteria. The effect of ingredients on phagocytosis activity can be measured ex vivo with fresh blood of healthy human volunteers after incubation with FITC-labelled *E. coli* bacteria. The percentage of phagocytosing cells in the granulocyte population can be determined by flow cytometry. The results are typically normalized to the effect of lipo-polysaccharide (LPS), which is a well known potent immunostimulating reference compound. Suitably, a normalized percentage phagocytosing granulocytes of more than 40% is regarded as a significant immune stimulating effect.

NK cells can kill target cells that have lost or express insufficient amounts of MHC class I, a frequent event in tumor- or virus-infected cells. The effect of ingredients on NK cell activity can ex vivo be measured with peripheral blood mononuclear cells (PBMC) isolated from fresh blood of healthy human volunteers. After pre-incubation of the PBMCs with the ingredient, pre-labelled K562 target cells are usually added and after subsequent incubation, propidium iodide can be added for detection of dead cells. The percentage of dead target cells can be determined with flow cytometry. The results are typically normalized to the effect of interleukin-2 (IL-2), which is a well known potent NK cell stimulating reference compound. Suitably, a normalized % NK cell activity of more than 17% is regarded as a significant immune stimulating effect.

Pectin and Rhamnogalacturonan Polysaccharides

Pectin is a complex mixture of colloidal polysaccharides found in the primary cell walls of both monocotyledons (monocots) and dicotyledons (dicots). It is characterized by the presence of rhamnosyl, galacturonyl acid, arabinosyl, and galactosyl residues as the main components, and at least occasionally xylosyl, mannosyl, glucosyl and apiosyl residues. Traditionally, pectin is known for its gelling and viscosifying properties utilized in industrial and household preparations of jellies, jam, and marmalade and it is widely used for its thickening and viscosifying properties. Pectin is generally regarded to be poly-D-galacturonic acid (homogalacturonan, HG), wherein the galacturonyl acid moieties are linked via alpha(1-4) linkages. The carboxyl group of a galacturonyl acid residue may be esterified with methanol, to create high methoxy and low methoxy pectins. The degree of methyl esterification influences the gelling behaviour of pectin. Moreover the galacturonic acid may be acetylated, in addition to the methyl esters. In that case one of the hydroxyl groups 2-OH and 3-OH positions are substituted by esterification to yield the acetates. Acetylation generally prevents gel-formation but increases the stabilising and emulsifying effects of pectin. Pectic polysacchariride is a heterogenous group of polysaccharides including various amounts of various components sometimes present or absent such as (i) homogalacturonan (HG), (ii) xylogalacturonan (XGA), (iii) rhamnogalacturonan-I backbone, encompassing arabinan and arabinogalactan I and II side-chains (RG-I), and (iv) rhamnogalacturonan-II (RG-II) (Ralet et al., Carbohydrate Research, vol. 344, 2009, p. 1798-1807). Pectic polysaccharide composition and fine structure vary widely depending on the plant source and the extraction conditions applied. The poly-GalA core can have a length of about 100 consecutive D-GalA residues. The RG-I core containing the side chains is usually called the 'ramified region' or 'hairy region', while the poly-GalA core (between 2 RG-I cores) is not typically substituted with oligosaccharides.

Rhamnogalacturonans are a group of closely related cell wall pectic polysaccharides that contain a backbone of the repeating disaccharide:
[→4)-D-GalA-alpha(12)-L-Rha-alpha(1→]
(which can also be represented as: [-4)-D-GalA-alpha(1-2)-L-Rha(p)-alpha(1-])

Rhamnogalacturonan-I (RG-I) is referred to as regions with 30-40 repeats of GalA and rhamnose (Rha) pairs [Westereng 2009 ibid.], with varying numbers of Rha residues. The GalA residues are linked to the Rha residues via the 1 and 4 positions, while the Rha residue is linked to the GalA residue via the anomeric and 2-OH positions. In general about 20-80% of the Rha residues is branched at the 4-OH position (depending on the plant source and the method of isolation), with neutral and acidic side chains (or 4-OH position). These side chains consist mainly of Ara and Gal residues linked in various manners, constituting polymers known as arabinogalactan I (AG-I) and/or AG-II. AG-I is composed of a beta (1,4)-linked D-Gal backbone with substitutions at 3-OH of alpha-L-arabinosyl groups; the Gal backbone can have interspacing alpha(1,5)-L-Ara units. AG-II consists of highly ramified galactan with predominantly interior beta(1,3)-linked D-Galp with substitutions of short (1,6)-linked chains exteriorly. The latter has further attachments of (1,3)- and/or alpha(1,5)-linked L-Ara. The oligosaccharide side chains may be linear or branched, and some of these side chains may be terminated with alpha-L-fucosides, beta-D-glucuronides, and 4-O-methyl beta-D-glucuronyl residues.

Polysaccharide of the Invention

In a first aspect the present invention provides a polysaccharide obtained from plants of the species *Camellia sinensis*, wherein the backbone of the polysaccharide comprises alternating rhamnogalacturonan-I cores and alpha(1,4)-linked polygalacturonic acid or alpha(1,4)-linked oligogalacturonic acid cores, wherein the molar ratio of galacturonyl acid residues to rhamnosyl residues in the backbone of the polysaccharide ranges from 2.5:1 to 1:1, and wherein the polysaccharide has a molecular weight of at least 70 kDa.

The species *Camellia sinensis*, commonly known as the tea plant, belongs to the Theaceae family. Preferably the polysaccharide is obtained from the leaves of this plant.

The molar ratio of galacturonyl acid residues to rhamnosyl residues refers to the total number of residues of galacturonyl acid present in the polysaccharide according to the invention. Consequently this includes both the GalA residues present in the RG-I core linked to Rha residues, as well as the GalA residues present in the alpha(1,4)-linked polygalacturonic acid or alpha(1,4)-linked oligogalacturonic acid cores, hence linked to other GalA residues. Polygalacturonic acid is considered to be a (part of a) polymer of at least 10 galacturonyl acid residues linked to each other; oligogalacturonic acid is considered to be a (part of a) molecule of 2 to 10 galacturonyl acid residues linked to each other.

For example if the molar ratio of galacturonyl acid residues to rhamnosyl residues is 2:1, then the polysaccharide contains per rhamnosyl residue (which is present in the RG-I core) one corresponding GalA residue (which is also present in the RG-I core linked to a Rha residue), as well as one GalA residues in the alpha(1,4)-linked polygalacturonic acid or alpha(1,4)-linked oligogalacturonic acid core.

If, for example, the molar ratio of galacturonyl acid residues to rhamnosyl residues is 1:1, then the polysaccharide contains per rhamnosyl residue (present in the RG-I core) one corresponding alpha(1,2)-linked GalA residue (also present in the RG-I core linked to a Rha residue). In that case the polysaccharide does not contain GalA residues from the alpha(1,4)-linked polygalacturonic acid or alpha(1,4)-linked oligogalacturonic acid core.

Preferably the polysaccharide according to the first aspect of the invention is a polysaccharide wherein the molar ratio of galacturonyl acid residues to rhamnosyl residues in the backbone of the polysaccharide ranges from 2:1 to 1:1, preferably from 1.5:1 to 1:1. Even more preferred the molar ratio of galacturonyl acid residues to rhamnosyl residues in the backbone of the polysaccharide ranges from 1.2:1 to 1:1. In case the molar ratio is 1:1 or close to 1:1, the polysaccharide consists entirely or nearly entirely of an RG-I core, without or a very low proportion of alpha(1,4)-linked polygalacturonic acid or alpha(1,4)-linked oligogalacturonic acid cores.

The length of a RG-I core preferably ranges from 10 to 60 disaccharide units, wherein a disaccharide unit contains a rhamnosyl and a galacturonyl acid residue (as explained before). Preferably the length of the RG-I core is between 20 and 50, more preferably between 20 and 40 disaccharide units.

All polymers according to the invention modulate immune response, preferably stimulate immune response. Preferably with increasing molecular weight, the modulation of the immune response increases as well per weight amount of polysaccharide. The molecular weight of the polysaccharide according to the invention is at least 70 kDa. Preferably the polysaccharide according to the first aspect of the invention has a molecular weight between 70 and 2,000 kDa. The polysaccharide according to the invention preferably has a molecular weight between 70 and 110 kDa, more preferably between 110 and 2,000 kDa. Suitably the polysaccharide according tot the invention has a molecular weight between 110 and 1,000 kDa, preferably between 110 and 500 kDa, or between 500 and 1,000 kDa.

Preferably the polysaccharide according to the invention comprises is a polysaccharide wherein said rhamnogalacturonan-I core comprises one or more side chains, wherein the one or more side chains comprise a backbone of at least one or more alpha(1,5)-linked arabinosyl residues and wherein the one or more side chains are substituted at the 4-OH position of the rhamnosyl residues. Said preferred side chain comprising alpha(1,5)-linked arabinosyl residues may be substantially linear or branched. In case that side chain is primarily linear, the side chain primarily comprises alpha(1,5)-linked arabinosyl residues, which form the backbone of the side chain. In case said side chain is a branched side chain, then one or more alpha-arabinosyl residues are linked to the 2-OH and/or 3-OH to the of alpha(1,5)-linked arabinans.

The preferred molecular weight of the preferred side chain comprising an alpha(1,5)-linked arabinosyl residue can be expressed as a relative number: the molar ratio between the number of arabinosyl residues and the number of rhamnosyl residues. If the polysaccharide of the invention comprises a side chain comprising an alpha(1,5)-linked arabinosyl residue, then preferably the molar ratio of arabinosyl residues to rhamnosyl residues is between 50:1 and 1:2, more preferably between 40:1 and 1:2, more preferably between 30:1 and 1:2, more preferably between 20:1 and 1:2, more preferably between 20:1 and 1:1, and more preferably between 20:1 and 2:1. Alternatively, preferably the ratio is between 10:1 and 1:2, preferably between 6:1 and 1:2, preferably between 4:1 and 1:2.

If side chains comprising arabinosyl monomers are present, the length of the side chains (expressed as number of monomer units) preferably is between 1 and 100 monomer units, more preferably between 1 and 50 units, even more preferably between 1 and 30 units.

Another preferred polysaccharide according to the invention is a polysaccharide wherein said rhamnogalacturonan-I core comprises one or more side chains, wherein the one or more side chains comprise a backbone of at least one or more beta(1,4)-linked galactosyl residues and wherein said one or more side chains are substituted at the 4-OH position of the rhamnosyl residues. If the preferred polysaccharide according to the invention comprises a side chain comprising one or more beta(1,4)-linked galactan residues, then the side chain is mostly a linear unsubstituted chain. Preferably other galactans like beta(1,3)-linked galactan and/or beta(1,6)-linked galactan are absent, or at least substantially absent, which means that preferably less than 10 mol % of galactan residues are present in side chains are beta(1,3)-linked or beta(1,6)-linked galactan residues, preferably less than 5 mole %, preferably less than 2 mole %, preferably less than 1 mole %.

The preferred molecular weight of the preferred side chain comprising a beta(1,4)-linked galactan residue can be expressed as a relative number: the molar ratio between the number of galactosyl residues and the number of rhamnosyl residues. If the polysaccharide of the invention comprises a side chain comprising a beta(1,4)-linked galactan residue, then preferably the molar ratio of galactosyl residues to rhamnosyl residues is between 80:1 and 1:1, more preferably between 60:1 and 1:1, more preferably between 50:1 and 1:1, more preferably between 30:1 and 1:1, more preferably between 20:1 and 1:1, more preferably between 20:1 and 2:1, and more preferably between 20:1 and 3:1. Alternatively, preferably the ratio is between 30:1 and 1:2, preferably between 25:1 and 1:1, preferably between 20:1 and 1:1, preferably between 10:1 and 2:1, preferably between 6:1 and 2:1.

If side chains comprising galactosyl monomers are present, the length of the side chains (expressed as number of monomer units) preferably is between 1 and 100 monomer units, more preferably between 1 and 50 units, even more preferably between 1 and 30 units.

If the polysaccharide according to the invention comprises side chains which are substituted at the 4-OH position of rhamnosyl residues of the rhamnogalacturonan-I core, then preferably at most 5% of the side chains are arabinogalactan side chains, more preferably at most 1% of the side chains are arabinogalactan side chains. This should be understood to mean that preferably the polysaccharide according to the invention is substantially free from arabinogalactan side chains, more preferably free from arabinogalactan side chains. Arabinogalactan side chains are side chains which comprise both arabinosyl and galactosyl residues. Arabinogalactan I (AGI) and AGII have been described above.

Preferably the RG-I core of the polysaccharide of the invention comprises side chains, such that at least 20 mole % of the rhamnosyl residues is substituted at the 4-OH position, preferably at least 30 mole %, preferably at least 40 mole %, preferably at least 45 mole %, and preferably at most 90 mole %, preferably at most 80 mole %.

Preferably, in general the polysaccharide according to the invention has a small, even if any, effect on viscosity or thickening of liquid compositions when dissolved, as compared to standard pectins. With increasing molecular weight, the thickening effect preferably increases per unit weight, however this thickening effect preferably is still small. Preferably the effect as a thickener depends on the degree of branching of possible side chains and/or the average length of side chains of the RG-I core: with increasing branching and/or increasing average length of side chains, the thickening effect becomes less.

The polysaccharide according to the invention comprises residues of the monomers rhamnose, galacturonic acid, and if the polymer comprises one or more side chains, then the polysaccharide may contain residues of arabinose and/or galactose as well. In addition the polysaccharide may contain minor amounts of residues of the monomers fucose, glucose, glucuronic acid, xylose, and/or uronic acid. These monomers may for instance terminate side chains, if these are present. In a preferred embodiment the invention is directed to polysaccharides comprising xylose.

The methods for determining the structures of the polysaccharides of the present invention are known to the skilled person. These methods include analysis using $^1$H and $^{13}$C NMR.

Preferably the polysaccharide according to the first aspect of the invention or a preparation obtained from plants of the species *Camellia sinensis* comprising a polysaccharide according to the first aspect of the invention is for modulating immune response. Preferably the polysaccharide according to the invention or a preparation obtained from plants of the species *Camellia sinensis* comprising a polysaccharide according to the first aspect of the invention is suitable for modulating immune response, more preferably suitable for stimulating immune response. Preferably the polysaccharide according to the invention or a preparation obtained from plants of the species *Camellia sinensis* comprising a polysaccharide according to the first aspect of the invention is suitable for modulating immune response in animals or humans, more preferably in humans. A suitable method for intake of the polysaccharides or the said preparation according to the invention may be oral intake, for instance by intake of an edible product or pharmaceutical composition. Alternatively the polysaccharide or the said preparation may be taken in as ingredients in a pharmaceutical composition which is common in the field. Differences may exist between immunomodulating effects between different animal species including humans. The immunological effects in the present invention have been established using human immune cells and are therefore most pertinent to immunomodulation in humans and related mammals.

The polysaccharide is obtained from plants of the species *Camellia sinensis*, in order to provide a preparation comprising a polysaccharide according to the first aspect of the invention. The preparation may be obtained by a method as described herein below. Such a preparation is enriched in the polysaccharide of the invention, in comparison to the vegetable material from which the polysaccharide is extracted and/or derived. Such a preparation preferably contains between 0.5% and 99% of polysaccharide by weight of the preparation.

The physiological immune response of a consumer that consumes the polysaccharide according to the first aspect of the invention, may be determined by ex vivo analysis of the activity of phagocytic and natural killer (NK) cells of that consumer. The immune modulating response upon ingestion of the polysaccharides according to the invention generally occurs within a few hours, e.g. 2 or 3 hours. The effect may last for about 24 hours or longer. Suitably, upon continued consumption of products containing the polysaccharide according to the invention, for example once or twice a day at consecutive days, the immune response can be stimulated and prolonged, and the natural defence of the consumer against the flu or cold can be enforced.

The daily dose of a polysaccharide according to the invention required to obtain the preferred immune response modulating effect, preferably is between 1 and 10,000 milligram per day. More preferred the amount of polysaccharide dosed is between 5 and 10,000 milligram per day, preferably between 10 and 10,000 milligram per day, even more preferred between 10 and 5,000 milligram per day. More preferred the amount dosed is between 10 and 1,000 milligram per day and most preferred between 10 and 500 milligram per day. This amount may be dosed as a single dose per day, or as 2, 3, 4, 5, 6, 7, 8, 9, or 10 doses per day. Preferably the suitable amount of polysaccharides according to the invention are delivered by 1 or 2 doses per day.

Polysaccharide for Use as a Medicament

In a second aspect the present invention provides a polysaccharide according to the first aspect of the invention or a preparation obtained from plants of the species *Camellia sinensis* comprising a polysaccharide according to the first aspect of the invention for use as a medicament. More specifically the polysaccharide according to the first aspect of the invention or a preparation obtained from plants of the species *Camellia sinensis* comprising a polysaccharide according to the first aspect of the invention is for modulating immune response, preferably for increasing immune response. Such a medicament may be used in the treatment of a patient in order to recover from a disease such as the common cold, and also by a consumer to prevent from becoming ill or catching a cold. A medicament in the sense of the present invention should be explained to be a broad term, and encompasses, but is not limited to, prescription drugs, non-prescription drugs, over the counter medicines, dietary supplements, dietary foods, clinical foods, edible products, tablets, capsules, pills, and food products such as beverages or any other suitable food product, and any other composition which is commonly known to the skilled person. Alternatively the medicament may be an injectable substance or an inhalable substance, such as a nasal spray.

Preferably the polysaccharide according to the first aspect of the invention is for use in therapy or treatment. The therapy or treatment may involve not only treatment of a person in the classical sense, meaning treatment of a patient in order to recover from a disease. Treatment also includes prophylaxis, meaning preventing that a consumer becomes ill, or catches a cold or the flu. The present invention provides the use of a polysaccharide according to the first aspect of the invention or a preparation obtained from plants of the species *Camellia sinensis* comprising a polysaccharide according to the first aspect of the invention as a medicament. The present invention provides the use of a polysaccharide according to the first aspect of the or a preparation obtained from plants of the species *Camellia sinensis* comprising a polysaccharide according to the first aspect of the invention, to modulate immune response, preferably stimulate immune response. This way individuals suffering from a cold or flu may be treated to recover earlier than without treatment, and/or this way individuals may decrease the chance that they catch a cold or the flu. The present invention provides a method for treatment of a cold or the flu by administration of the polysaccharide according to the first aspect of the invention or by administration or a preparation obtained from plants of the species *Camellia sinensis* comprising a polysaccharide according to the first aspect of the invention.

The preferred dosage of the polysaccharide has already been indicated in the context of the first aspect of the invention, and is applicable to the second aspect of the invention as well.

In a third aspect the present invention provides a polysaccharide according to the first aspect of the invention or a preparation obtained from plants of the species *Camellia sinensis* comprising a polysaccharide according to the first aspect of the invention for use as a medicament to modulate immune response. This use preferably involves modulating immune response in humans or may also involve veterinary use, thus modulating immune response in animals, preferably mammals. Preferably the polysaccharide according to the first aspect of the invention is for use as a medicament to stimulate immune response in humans or animals, more preferred for stimulating the immune response in humans.

The polysaccharide according to the first aspect of the invention or a preparation obtained from plants of the species *Camellia sinensis* comprising a polysaccharide according to the first aspect of the invention is suitable to be used as a medicament to modulate immune response, preferably in humans. Preferably the polysaccharide is suitable to be used as a medicament to modulate immune response in animals, preferably mammals, thus in veterinary use. Preferably intake of the medicament leads to stimulation of the immune response, meaning that the immune system is enforced and better able to defend the animal or human body against unwanted intruders. Such a medicament may be used in the treatment of an animal or a human being in order to recover from a disease such as the common cold, and also by an animal or a human being to prevent becoming ill or catching a cold.

Preferably the present invention provides the use of a polysaccharide according to the first aspect of the invention or a preparation obtained from plants of the species *Camellia sinensis* comprising a polysaccharide according to the first aspect of the invention for the manufacture of a medicament to modulate immune response in animals or humans, preferably humans. Preferably the present invention provides the use of a polysaccharide according to the first aspect of the invention or a preparation obtained from plants of the species *Camellia sinensis* comprising a polysaccharide according to the first aspect of the invention for the manufacture of a medicament to stimulate immune response in animals or humans, preferably humans.

The preferred dosage of the polysaccharide has already been indicated in the context of the first aspect of the invention, and is applicable to the third aspect of the invention as well.

Among the general public there is a desire to increase the natural defence of the human body against intruders which may cause a cold or the flu, or any other symptom which causes the consumer to feel weak or ill. The present invention is preferably directed to protection of a) the mouth and larynx against e.g. localized and/or respiratory or middle ear infections and/or b) the gastrointestinal tract, against gastrointestinal tract infections. The infections are typically caused by viruses or bacteria. This is especially relevant for subjects with a suboptimal immune defence against such pathogens, for instance because of impaired NK cell function. Impaired NK cell function has been associated with increased susceptibility to such common infections and has been well documented in elderly subjects as well as in subjects experiencing physiological (e.g. strenuous exercise, shift working, sleep deprivation) or psychological (e.g. exam stress, preparing for a wedding, loss of a relative, caring for a chronically ill relative) stress.

The invention is directed to the prophylaxis of individuals in need of modulation of their immune responsiveness. The invention is especially suitable to enhance the immune response to pathogens or antigens in subjects with a (partially) suboptimal immune responsiveness due to e.g. age-, diet-, or life-style associated impairment of immune function. Application of the structures as described in the present invention can be used to support their immune system to mount an adequate response and thus increase the subject's resistance to common infections, enhance their response to a vaccine and in other applications reduce inflammatory and for allergic conditions.

Preferably the polysaccharide according to the invention or a preparation obtained from plants of the species *Camellia sinensis* comprising a polysaccharide according to the first aspect of the invention is used as an adjuvant for vaccines. Preferably the polysaccharide according to the invention is used as an adjuvant for vaccines. Most vaccines in use today employ killed or attenuated microbes or microbial fragments to stimulate a protective immune response against the cognate infectious agent. However, problems associated with the manufacture of conventional vaccines has led to the development of more defined synthetic antigens using chemical and recombinant techniques. These defined antigens by themselves have a lower potency and immunogenicity and typically need to be combined with an adjuvant to form an effective vaccine. An adjuvant is an agent that stimulates the immune system and increases the response to an antigen, without having a specific antigenic effect in itself (M. Singh (ed.), Vaccine adjuvants and delivery systems, Wiley-Interscience 2007). The polysaccharide according to the invention may be combined with a specific antigen in a vaccine to increase the immune response against the antigen, in order to improve the functionality of the vaccine. For this use the antigenic material of a vaccine is combined with an amount of polysaccharide according to the invention that stimulates the initiation of a specific adaptive immune response against the specific antigen(s) without inducing overt adverse responses. Other additives as established in the field may be added to the vaccine for instance to serve as a carrier, a depot or a preservative. The polysaccharide according to the invention may be used in vaccines for veterinary or human use and in vaccines for different application routes including vaccines that are injected (e.g diphtheria, pertussis, tetanus, polio, smallpox, influenza, and pneumococcal polysaccharide), vaccines that are applied orally (e.g. polio, rotavirus) or that are applied nasally (e.g. influenza).

The invention revealed that the materials of the present invention are highly active in immune modulation, preferably immune stimulation. The invention revealed that the novel polysaccharides are active with regard to human immune cells (especially under conditions of examples with phagocytosis or NK cell activation), depending on the selected process, at concentrations of at or below 300 microgram per milliliter, more preferably 100 microgram per milliliter, more preferably 50 microgram per milliliter, more preferably 30 microgram per milliliter, even more preferably 10 microgram per milliliter, even more preferably 3.0 microgram per milliliter, even more preferably 1.0 microgram per milliliter, even more preferably 0.3 microgram per milliliter.

Edible Product or Pharmaceutical Composition

In a fourth aspect the present invention provides an edible product or pharmaceutical composition comprising a polysaccharide according to the first aspect of the invention or a preparation obtained from plants of the species *Camellia sinensis* comprising a polysaccharide according to the first aspect of the invention. Preferably the edible product or pharmaceutical composition is suitable for modulating immune response, more preferably suitable for stimulating immune response, upon intake by any suitable method.

Depending on the specific edible product or pharmaceutical composition, the edible product or pharmaceutical composition according to the invention preferably comprises from an edible product or pharmaceutical composition according to the fourth aspect of the invention, comprising from 0.0001 to 25% by weight of the polysaccharide, more preferred from 0.0002 to 10% by weight. Preferably the concentration of the polysaccharide in the composition according to the invention is between 0.5% and 10% by weight, preferably between 1% and 10% by weight, more preferred between 2% and 10% by weight, more preferred between 3% and 10% by weight, more preferred between 4% and 10% by weight, and most preferred between 5% and 9% by weight. The polysaccharides according to the invention may be present in the edible product or pharmaceutical composition in its native form, meaning as a constituent of a vegetable material which is used in the edible product or pharmaceutical composition. Nevertheless preferably the edible product or pharmaceutical composition is enriched with the polysaccharide according to the invention. This means that the polysaccharide is possibly not only present in its native form as a constuent of a vegetable material, but that in addition also the polysaccharide is added as an ingredient to the edible product or pharmaceutical composition. The polysaccharide may be added in pure form or as part of an extract enriched in the polysaccharide or in any other suitable form. Hence preferably, the edible product or pharmaceutical composition according to the invention preferably comprises from 0.0001 to 25% by weight of the polysaccharide, wherein at least a part of the polysaccharides is added to the edible product or pharmaceutical composition in an enriched form. Preferably the concentration of the polysaccharide in the composition according to the invention is between 0.5% and 10% by weight, preferably between 1% and 10% by weight, more preferred between 2% and 10% by weight, more preferred between 3% and 10% by weight, more preferred between 4% and 10% by weight, and most preferred between 5% and 9% by weight, wherein at least a part of the polysaccharides is added to the edible product or pharmaceutical composition in an enriched form. The polysaccharides according to the invention may be added to the edible product or pharmaceutical composition in a specific salt form.

The edible product according to the present invention may take any physical form. In particular, it may be a food product, a beverage, a dietary food product, or a clinical food product. It may also be a dietary supplement, in the form of a beverage, a tablet, a capsule, or any other suitable form for a dietary supplement. Preferred edible products for incorporation of the polysaccharide according to the invention are in the form of a liquid, such as a soup or a beverage, a spread, a dressing, a dessert or a bread. If the preferred edible product is a soup, this may be a liquid soup, or a dried soup to which hot water can be added by the consumer. The edible product may be in liquid or spreadable form, it may be a spoonable solid or soft-solid product, or it may be a food supplement. Preferably the edible product is a liquid product. The edible product may suitably take the form of e.g. a soup, a beverage, a spread, a dressing, a dessert, a bread. More preferably, the edible product is a beverage, a dessert or a spread. More preferably, the edible product is a beverage or a spread, especially a spread in the form of an oil-in-water emulsion or a water-in-oil emulsion. The term 'spread' as used herein encompasses spreadable products such as margarine, light margarine, spreadable cheese based products, processed cheese, dairy spreads, and dairy-alternative spreads. Spreads as used herein (oil-in-water or water-in-oil emulsions) may have a concentration of oil and/or fat of between about 5% and 85% by weight, preferably between 10% and 80% by weight, more preferred between 20% and 70% by weight. Preferably the oil and/or fat are from vegetable origin (such as but not limited to sunflower oil, palm oil, rapeseed oil); oils and/or fats of non-vegetable origin may be included in the composition as well (such as but not limited to dairy fats, fish oil).

Most preferably, the product is a beverage. Such a beverage typically contains at least 60% by weight water and 0 to 20% by weight of dispersed oil or fat. Preferably, such beverage contains at least 70% by weight water and 0 to 10% by weight of dispersed oil or fat.

A dressing in the context of the present invention generally is an oil-in-water emulsion, which may contain between 0.1 and 85% of oil and/or fat. Mayonnaise is an example of a dressing within the context of the present invention. Dressings as used herein (oil-in-water emulsion) may have a concentration of oil and/or fat of between about 50.1 and 85% by weight, preferably between 5% and 80% by weight, more preferred between 10% and 70% by weight. Preferably the oil and/or fat are from vegetable origin (such as but not limited to sunflower oil, palm oil, rapeseed oil); oils and/or fats of non-vegetable origin may be included in the composition as well (such as but not limited to dairy fats, fish oil).

A pharmaceutical composition in the context of the present invention encompasses, but is not limited to, prescription drugs, non-prescription drugs, over the counter medicines, dietary supplements, dietary foods, clinical foods, edible products, tablets, capsules, pills, and food products such as beverages or any other suitable food product, and any other composition which is commonly known to the skilled person. Alternatively the medicament may be an injectable substance or an inhalable substance, such as a nasal spray. In case of a pharmaceutical composition, the composition may contain more than 25% by weight of the polysaccharide according to the invention, preferably more than 30% by weight, preferably more than 40% by weight, or preferably more than 50% by weight, or preferably even more than 75% by weight.

Edible products suitable for this invention can be any food product, including beverages, dietary food products and clinical food products. The concentration of the polysaccharide according to the invention should be such that modulation of the immune response occurs after consumption of the food product at a regular amount. A regular amount is the amount that an average consumer consumes of such a food product at a specific consumption moment.

The preferred daily dose of the polysaccharides according to the first aspect of the invention has been indicated above, and is applicable to the fourth aspect of the invention as well. The concentration of polysaccharides required in the edible product depends on the specific edible product and how much of such a product is usually consumed. Preferably the polysaccharides according to the invention are incorporated in edible products which are usually consumed at a predefined amount. For example a cereal bar is usually packed per single bar, and also consumed per single bar. Usually the weight of such a bar is between 40 and 80 gram. Similarly, dairy mini-drinks are consumed from small bottles, having a volume of about 100 milliliter.

By incorporating the polysaccharides in such food products, the daily intake of the polysaccharides can in principle be controlled. Preferably the polysaccharides are delivered to the consumer in 1 or 2 doses per day. The skilled person is able to calculate the required concentration of the polysaccharide in a unit amount of the edible product, preferably food product.

A unit amount of a food product is a quantity of a food product which is usually consumed as a single serving. The unit amount or serving size of such food products depends on the specific product. A few non-limiting examples of typical serving sizes are:
milk, yoghurt: 200 mL
natural cheese: 43 gram
processed cheese: 57 gram
fruit juice: 177 mL
soft drink: 200 mL
bread: 1 slice, 35 gram
coffee: 125 mL
tea: 150 mL
cereal bar, candy bar: 50 gram
chocolate: 30 gram
ice cream: 100 mL
spread: 15 gram
soup: 250 mL
cocoa beverage: 200 mL A unit amount of a food product in the context of the present invention may be packed and sold as a single portion. For example, ice cream may be packed as individual units, therewith making such an individual portion a unit amount in the context of the present invention. The actual weight or volume of such an individually packed product may be higher or lower than indicated above for a standard serving size. For example probiotic dairy drinks are consumed from small bottles, individually packed, having a volume of about 100 mL.

Combinations of Polysaccharides Obtained from Various Species

Also an edible product or pharmaceutical composition that contains a polysaccharide obtained from plants of the species *Camellia sinensis* according to the first aspect of the invention, or a preparation obtained from plants of the species *Camellia sinensis* comprising a polysaccharide according to the first aspect of the invention, in combination with one or more polysaccharides obtained from other species are within the scope of the present invention. Hence the present invention provides an edible product or pharmaceutical composition comprising a polysaccharide according to the first aspect of the invention, and additionally a polysaccharide that is obtained from one or more other vegetable materials. Preferably the vegetable materials belong to the following families:

Apiaceae family, preferably chosen from the group of species consisting of *Petroselinum crispum, Apium graveolens, Pastinaca sativa*, and *Daucus carota*;

and/or the Fabaceae family, preferably from plants of the species *Glycine max*;

and/or the Rosaceae family, preferably from plants of the species *Malus domestica*;

and/or the Chenopodiaceae family, preferably from plants of the species *Beta vulgaris* L.;

and/or the Asteraceae family, preferably from plants of the species *Helianthus tuberosus*.

Polysaccharides from Apiaceae Family

In addition to the polysaccharide according to the first aspect of the invention, preferably the edible product or pharmaceutical composition according to the fourth aspect of the invention comprises polysaccharides that are obtainable from one or more plants belonging to the Apiaceae family, preferably from plants of the species *Daucus carota*. Alternatively the polysaccharide is obtainable from the group of species consisting of *Petroselinum crispum, Apium graveolens, Pastinaca sativa*, and *Daucus carota*. Also combinations of these species are possible. Most preferably the polysaccharide is obtainable from the species *Daucus carota* subsp. *sativus*. Most preferred the polysaccharide is obtainable from the root of the species *Daucus carota* subsp. *sativus*.

Many plants from the family Apiaceae are edible. Examples of genuses from this family are *Daucus, Angelica*, and *Bupleurum*. The best-known species of *Daucus* is the cultivated carrot, *Daucus carota* subsp. *sativus*. *Angelica* is a genus of about 60 species of biennial and perennial herbs, and mainly used medicinally today for bronchial and digestive problems. *Bupleurum* is a large genus, containing about 190 species.

The polysaccharides are preferably obtainable from plants of the species *Petroselinum crispum*, which is known as the herb parsley. This species belongs to the Apiaceae family. In a preferred embodiment the polysaccharide is obtainable from the species *Petroselinum crispum* var. *tuberosum*, which is known as hamburg root parsley, an example of a heirloom food product.

In another preferred embodiment, the polysaccharide is obtainable from plants of the species *Apium graveolens*. This species belongs to the Apiaceae family. Especially preferred are polysaccharides obtainable from the species *Apium graveolens* var. *rapaceum*, which is known as celeriac. This root vegetable is also an example of a heirloom food product. Especially preferred the polysaccharide is obtainable from the root of plant *Apium graveolens* var. *rapaceum*.

In another preferred embodiment, the polysaccharide is obtainable from plants of the species *Pastinaca sativa*. This species belongs to the Apiaceae family. Especially preferred are polysaccharides obtainable from the species *Pastinaca sativa* subsp. *sativa*, which is known as parsnip. This root vegetable is also an example of a heirloom food product. Especially preferred the polysaccharide is obtainable from the root of the plant *Pastinaca sativa* subsp. *sativa*.

In another preferred embodiment, the polysaccharide is obtainable from plants of the species *Daucus carota*. This species belongs to the Apiaceae family, and this species includes wild carrot, of which the root is edible. More preferably the polysaccharide is obtainable from the species *Daucus carota* subsp. *sativus*, which is called the commonly cultivated carrot. The carrot is a well known root vegetable, usually orange, red, purple, white or yellow in colour.

When the edible product or pharmaceutical composition according to the invention comprises polysaccharides which are obtainable from the species *Daucus carota* subsp. *sativus*, more preferably from the root of the species *Daucus carota* subsp. *sativus* (from carrot), then the molar ratio of galacturonyl acid residues to rhamnosyl residues in the backbone of the polysaccharide ranges from 1.5:1 to 1:1, preferably from 1.2:1 to 1:1.

Preferably the polysaccharide has a molecular weight of at least 110 kDa, most preferably between 110 and 2,000 kDa.

Preferably the polysaccharide according to the invention that is obtainable from *Daucus carota* subsp. *sativus*, contains side chains connected to the 4-OH position of the rhamnosyl residues, wherein the side chains comprise arabinosyl residues, and wherein the molar ratio of arabinosyl residues to rhamnosyl residues of the polysaccharide is between 50:1 and 5:1, more preferably between 30:1 and 5:1, most preferably between 20:1 and 5:1.

Preferably the polysaccharide according to the invention that is obtainable from *Daucus carota* subsp. *sativus*, contains side chains connected to the 4-OH position of the rhamnosyl residues, wherein the side chains comprises galactosyl residues, and wherein the molar ratio of galactosyl residues to rhamnosyl residues of the polysaccharide is between 50:1 and 5:1, more preferably between 30:1 and 5:1, most preferably between 20:1 and 5:1.

Preferably the number of side chains is such that at least 40 mole % of the rhamnosyl residues of the rhamnogalacturonan-I core is substituted, preferably at least 50 mole %, and preferably at most 90 mole %, more preferably at most 80 mole %.

In another preferred embodiment, when the edible product or pharmaceutical composition according to the invention comprises polysaccharides which are obtainable from the root of the species *Daucus carota* subsp. *sativus* (from carrot), then the molar ratio of galacturonyl acid residues to rhamnosyl residues in the backbone of the polysaccharide may range from 25:1 to 1:1, preferably from 20:1 to 1:1, more preferably from 20:1 to 10:1.

In that case, preferably the polysaccharide has a molecular weight between 70 and 110 kDa.

Moreover, the said polysaccharide obtainable from *Daucus carota* subsp. *sativus*, contains side chains connected to the 4-OH position of the rhamnosyl residues, wherein the side chains comprise arabinosyl residues, and wherein the molar ratio of arabinosyl residues to rhamnosyl residues of the polysaccharide is between 20:1 and 2:1, more preferably between 15:1 and 3:1, most preferred between 14:1 and 7:1.

Moreover, the said polysaccharide obtainable from *Daucus carota* subsp. *sativus*, preferably contains side chains connected to the 4-OH position of the rhamnosyl residues, wherein the side chains comprises galactosyl residues, and wherein the molar ratio of galactosyl residues to rhamnosyl residues of the polysaccharide is between 20:1 and 2:1, more preferably between 15:1 and 3:1, most preferred between 10:1 and 3:1.

Preferably the number of side chains is such that at least 50 mole % of the rhamnosyl residues of the rhamnogalacturonan-I core is substituted, preferably at least 60 mole %, and preferably at most 90 mole %, more preferably at most 80 mole %.

Polysaccharides from Fabaceae family

In another preferred embodiment, the invention provides an edible product or pharmaceutical composition according to the fourth aspect of the invention, comprising a polysaccharide according to the first aspect of the invention, and additionally a polysaccharide that is obtained from one or more plants belonging to the Fabaceae family, preferably from plants of the species *Glycine max*, commonly known as soya. Most preferably the polysaccharide is obtainable from the soyabean.

When the edible product or pharmaceutical composition according to the invention comprises polysaccharides which are obtainable from the species *Glycine max*, more preferably from soyabean, then the molar ratio of galacturonyl acid residues to rhamnosyl residues in the backbone of the polysaccharide ranges from 1.5:1 to 1:1, preferably from 1.2:1 to 1:1.

Preferably the polysaccharide has a molecular weight of between 70 and 2000 kDa, more preferably between 70 and 110 kDa, more preferably at least 110 kDa, most preferably between 110 and 2,000 kDa.

Preferably the polysaccharide according to the invention that is obtainable from *Glycine max*, contains side chains connected to the 4-OH position of the rhamnosyl residues, wherein the side chains comprises arabinosyl residues, and wherein the molar ratio of arabinosyl residues to rhamnosyl residues of the polysaccharide is between 50:1 and 1:2, more preferred between 40:1 and 1:1, and more preferred between 30:1 and 2:1, more preferred between 25:1 and 3:1.

Preferably the polysaccharide according to the invention that is obtainable from *Glycine max*, contains side chains connected to the 4-OH position of the rhamnosyl residues, wherein the side chains comprises galactosyl residues, and wherein the molar ratio of galactosyl residues to rhamnosyl residues of the polysaccharide is between 70:1 and 1:2, more preferred between 60:1 and 1:1, and more preferred between 50:1 and 2:1, more preferred between 40:1 and 5:1.

Preferably the number of side chains is such that at least 40 mole % of the rhamnosyl residues of the rhamnogalacturonan-I core is substituted, preferably at least 50 mole %, and preferably at most 90 mole %, preferably at most 80 mole %.
Polysaccharides from Rosaceae Family In another preferred embodiment, the invention provides an edible product or pharmaceutical composition according to the fourth aspect of the invention, comprising a polysaccharide according to the first aspect of the invention, and additionally a polysaccharide that is obtained from one or more plants belonging to the Rosaceae family, preferably from plants of the species *Malus domestica*, commonly known as the apple. Most preferably the polysaccharide is obtainable from the fruit of the species *Malus domestica*, which is the commonly known apple.

When the edible product or pharmaceutical composition according to the invention comprises polysaccharides which are obtainable from the species *Malus domestica*, more preferably from the apple, then the molar ratio of galacturonyl acid residues to rhamnosyl residues in the backbone of the polysaccharide ranges from 1.5:1 to 1:1, preferably from 1.2:1 to 1:1.

Preferably the polysaccharide has a molecular weight of between 70 and 2,000 kDa, preferably between 70 and 110 kDa, preferably between 110 and 2,000 kDa.

Preferably the polysaccharide according to the invention that is obtainable from *Malus domestica*, contains side chains connected to the 4-OH position of the rhamnosyl residues, wherein the side chains comprises arabinosyl residues, and wherein the molar ratio of arabinosyl residues to rhamnosyl residues of the polysaccharide is between 10:1 and 1:2, preferably between 5:1 and 1:2.

Preferably the polysaccharide according to the invention that is obtainable from *Malus domestica*, contains side chains connected to the 4-OH position of the rhamnosyl residues, wherein the side chains comprises galactosyl residues, and wherein the molar ratio of galactosyl residues to rhamnosyl residues of the polysaccharide is between 10:1 and 1:2, preferably between 5:1 and 1:1.

Preferably the number of side chains is such that at least 50 mole % of the rhamnosyl residues of the rhamnogalacturonan-I core is substituted, preferably at least 60 mole %, and preferably at most 90 mole %, preferably at most 80 mole %.
Polysaccharides from Chenopodiaceae Family In another preferred embodiment, the invention provides an edible product or pharmaceutical composition according to the fourth aspect of the invention, comprising a polysaccharide according to the first aspect of the invention, and additionally a polysaccharide that is obtained from one or more plants belonging to the Chenopodiaceae family, preferably from plants of the species *Beta vulgaris* L. Most preferably the polysaccharide is obtainable from the root of the species *Beta vulgaris* L., which is the commonly known sugar beet.

When the edible product or pharmaceutical composition according to the invention comprises polysaccharides which are obtainable from the species *Beta vulgaris* L., more preferably from the root of *Beta vulgaris* L. (sugar beet), then the molar ratio of galacturonyl acid residues to rhamnosyl residues in the backbone of the polysaccharide ranges from 1.5:1 to 1:1, preferably from 1.2:1 to 1:1.

Preferably the polysaccharide has a molecular weight of at least 110 kDa, more preferred between 110 and 2,000 kDa.

Preferably the polysaccharide according to the invention that is obtainable from *Beta vulgaris* L., contains side chains connected to the 4-OH position of the rhamnosyl residues, wherein the side chains comprises arabinosyl residues, and wherein the molar ratio of arabinosyl residues to rhamnosyl residues of the polysaccharide is between 50:1 and 1:2, preferably between 40:1 and 1:1, more preferred between 35:1 and 5:1.

Preferably the polysaccharide according to the invention that is obtainable from *Beta vulgaris* L., contains side chains connected to the 4-OH position of the rhamnosyl residues, wherein the side chains comprises galactosyl residues, and wherein the molar ratio of galactosyl residues to rhamnosyl residues of the polysaccharide is between 10:1 and 1:2, preferably between 5:1 and 1:1.

Preferably the number of side chains is such that at least 40 mole % of the rhamnosyl residues of the rhamnogalacturonan-I core is substituted, preferably at least 50 mole %, and preferably at most 90 mole %, preferably at most 80 mole %.
Polysaccharides from Asteraceae Family In another preferred embodiment, the invention provides an edible product or pharmaceutical composition according to the fourth aspect of the invention, comprising a polysaccharide according to the first aspect of the invention, and additionally a polysaccharide that is obtained from one or more plants belonging to the Asteraceae family, preferably from plants of the species *Helianthus tuberosus*. This preferred species is also known as Jerusalem artichoke or topinambur.

Preferred food products according to the invention may be dried and contain less than 40% water by weight of the composition, preferably less than 25%, more preferably from 1 to 15%. Alternatively, the food may be substantially aqueous and contain at least 40% water by weight of the composition, preferably at least 50%, more preferably from 65 to 99.9%.

The food preferably comprises nutrients including carbohydrate (including sugars and/or starches), protein, fat, vitamins, minerals, phytonutrients (including terpenes, phenolic compounds, organosulfides or a mixture thereof) or mixtures thereof. The source of the protein material is not limited, and may for example be from dairy origin (such as casein, lactoglobulin), or vegetable origin (such as soya, pea, etcetera). The food may be low calorie (e.g. have an energy content of less than 100 kCal per 100 gram of the composition) or may have a high calorie content (e.g. have an energy content of more than 100 kCal per 100 g of the composition, preferably between 150 and 1000 kCal). The food may also contain salt, flavours, colours, preservatives, antioxidants, non-nutritive sweetener or mixtures thereof. Suitable vitamins and minerals include but are not limited to vitamin A, vitamin D, vitamin E, vitamin C, thiamin, riboflavin, niacin, vitamin B6, folate, vitamin B12 (cyanocobalamin), biotin, pantothenic acid, calcium, phosphorous, potassium, iron, zinc, copper, iodine, selenium, sodium, magnesium, manganese, molybdenum, vitamin K, chromium and mixtures thereof. The preferred ingredients to deliver vitamins and minerals include but are not limited to potassium phosphate, calcium phosphate, magnesium oxide, magnesium phosphate ascorbic acid, sodium ascorbate, vitamin E acetate, niacinamide, ferric orthophosphate, calcium pantothenate, zinc oxide, zinc gluconate, vitamin A palmitate, pyridoxine hydrochloride, riboflavin, thiamin mononitrate, biotin, folic acid, chromium chloride, potassium iodide, sodium molybdate, sodium selenate, phytonadone (vitamin K), cholecalciferol (vitamin D3), manganese sulfate and mixtures thereof. Preferably, the product according to the invention contains at least 10% or more of the recommended daily amount ('RDA') of the vitamins and minerals.

The products according to the invention may further include meat, fish, meat and fish extracts, fruit, dried fruit, fruit concentrates, fruit extracts, fruit juices, tea (e.g. green tea), vegetables, vegetable extracts and concentrates, nuts, nut extracts, chocolate, bread, vinegar, salt, pepper, cocoa powder, herbs (e.g. parsley), herb extracts, spices (e.g. cinnamon), spice extracts, emulsifiers, acidity regulators (e.g. phosphoric, malic, citric, tartaric acids and salts thereof), flavonoids, preservatives (e.g. lactic acid, EDTA, tocopherols, sodium benzoate), colours (e.g. beta carotene, lycopene, caramel, carmine red), fibers (e.g. soya), leavening agents (e.g., sodium bicarbonate), pectin, citric acid, yeast, salt, glycerin, and mixtures thereof.

The edible products or pharmaceutical compositions according to the invention may be prepared by any method which is common to the skilled person. Hence in a fifth aspect the present invention provides a method for preparation of an edible product or pharmaceutical composition comprising a polysaccharide according to the first aspect of the invention, or a preparation obtained from plants of the species *Camellia sinensis* comprising a polysaccharide according to the first aspect of the invention, wherein the polysaccharide is brought into contact with at least one ingredient of the edible product or pharmaceutical composition.

The polysaccharide according to the invention or a preparation obtained from plants of the species *Camellia sinensis* comprising a polysaccharide according to the first aspect of the invention may be incorporated into an edible product or pharmaceutical composition by bringing the polysaccharide in purified form into contact with other ingredients of the edible product or pharmaceutical composition. Additionally, or alternatively, a vegetable material that contains the polysaccharides according to the invention may be brought into contact with other ingredients of the edible product or pharmaceutical composition. These steps may be performed in any stage of the production process. For example, the polysaccharides may be mixed into a ready or nearly ready made edible product or pharmaceutical composition or it may be brought into contact with ingredients, such that the ingredients are subsequently mixed and the edible product or pharmaceutical composition is prepared.

Method for Isolation of the Polysaccharide

Finally in a sixth aspect the present invention provides a method for isolation of a polysaccharide according to the first aspect of the invention or a preparation obtained from plants of the species *Camellia sinensis* comprising a polysaccharide according to the first aspect of the invention, comprising the following steps:
1. preparation of an aqueous extract of a suitable vegetable material, at a temperature between 20 and 100° C., during a period of between 1 and 6 hours, to release the polysaccharide of invention from the vegetable material;
2. purification of the extracted polysaccharide according to the first aspect of the invention.

This aspect of the invention provides a method to obtain the polysaccharides which can be used to modulate immuno response.

In the first step of the method according to the sixth aspect of the invention, an aqueous extract of a suitable vegetable material is prepared at a temperature between 20 and 100° C., during a period of between 1 and 6 hours, to release the polysaccharide of invention from the vegetable material. Preferably the temperature during this pressure is atmospheric pressure, meaning about 101,325 bar at sea level. Natural variations in the pressure may occur due to weather conditions and altitude may occur and are within the scope of the invention. The aqueous extract is prepared by extracting the vegetable material with water by using preferably at least a threefold amount of water (w/w) of temperature between 20° C. and 100° C. at atmospheric pressure. Preferably the temperature at which the extraction is performed is at least 60° C., more preferred at least 70° C., more preferred at least 80° C. and most preferred at least 90° C. The extraction takes place during a period of at least 1 hour, preferably at least 1.5 hours, more preferably at least 2 hours. The extraction time is maximally 6 hours, more preferred maximally 5 hours. The extraction preferably is performed at the boiling temperature of water, meaning about 100° C. at atmospheric pressure. The extraction may also be performed at a pressure higher than atmospheric pressure, potentially leading to decreased extraction time. The advantage of a higher temperature is that the extraction of the polysaccharides is more rapid than at relatively low temperatures. On the other hand, undesired side reactions are to be avoided, hence the pressure at which the reaction is performed is preferably maximally atmospheric pressure. Additionally at temperatures from about 70° C., endogenous enzymes present in the plant material are generally deactivated, meaning that these enzymes do not exert any activity anymore.

In order to obtain the vegetable materials, this method according to the invention preferably also comprises a step wherein a plant and/or a plant organ is harvested, wherein the plant and/or plant organ comprises the polysaccharides according to the first aspect of the invention. In a further step preferably the harvested plant or plant organ is grinded or cut in parts or pieces, in order to optimise the extraction process. The vegetable material may be dried before being extracted; it may also be subjected to the process in native form, i.e. not dried.

The six major plant parts (in botanical context) are roots, stems, leaves, flowers, fruits, and seeds. The following plant organs are examples of organs which are suitable in the context of the present invention: leaves (defined as the plant organ specialised for photosynthesis), including needles; flowers and flower heads; buds; seeds; pods; fruits; tubers and roots; and stem.

Plants that are suitable as starting material for extraction of the additional polysaccharides according to the present invention include any plant, but especially preferred are edible plants or plant organs, as described by the general term 'fruit and vegetables'. A vegetable is a plant that is cultivated for an edible part, such as the root of a beet, the leaf of spinach, or the flower buds of broccoli or cauliflower. A vegetable is generally seen as any savoury or less sweet plant product. Usually in culinary context the term vegetable excludes sweet fruits, seeds, nuts, grains, and herbs and spices. The definition of fruit depends on whether the term is used in culinary or biological (or botanical) context. In culinary terms, fruit is usually a sweet tasting plant reproduction organ, like an apple, or strawberry. Some fruits in botanical sense are in culinary context seen as vegetables, because they are not (or less) sweet, for example cucumber and tomato.

Plants and/or vegetable materials especially suitable as source of the additional polysaccharides according to the invention have been indicated before. The organ of the plants which may contain the polysaccharides according to the invention depend on the actual species which is utilised as source of the polysaccharides. These organs may be any part of species, such as leaves (defined as the plant organ specialised for photosynthesis), including needles; flowers and flower heads; buds; seeds; pods; fruits; berries, tubers and roots, and the stem including the bark. For example, the following organs of the preferred species are preferred as source of the additional polysaccharides according to the invention:

*Daucus carota* subsp. *sativus* (carrot): the root;
*Glycine max* (soya): the bean, which is a seed;

*Malus domestica* (apple): the fruit, especially the skin of the fruit;
*Beta vulgaris* L. (sugar beet): the root;
*Helianthus tuberosus* (topinambur): the tuber.

Generally, plant-based polysaccharides consist of large insoluble polymers, like cell wall components, small soluble oligosaccharides, like monomers (e.g. glucose) and dimers (e.g. cellobiose), and large soluble polysaccharides. Hence, preferably prior to preparing the aqueous extract, the vegetable material is brought into contact with an alcohol or any other suitable organic solvent, wherein the alcohol preferably comprises ethanol. By this optional step, small organic molecules like mono- and disaccharides, small organic acids and their metal salts, amino acids and oligopeptides, polyphenols, color contributing molecules like carotenoids, anthocyanes and chlorophyll, and fatty substances like glycerides, cholines, phospholipids and steroids are removed, in order to increase the relative content of polysaccharides in the vegetable material which does not dissolve in the solvent.

Preferably this optional step is carried out at a temperature of between 60° C. and 80° C., during a period of between 15 minutes and 5 hours, preferably between 1 and 3 hours, preferably at atmospheric pressure. The solid residue which does not dissolve during this solvent extraction is separated from the liquid by any suitable method, such as filtration or centrifugation. The solids remaining after this separation step contain the polysaccharide of interest. Optionally a second extraction step wherein the solid material obtained after the first alcoholic extraction is brought into contact with an alcohol or any other suitable organic solvent, preferably comprising ethanol, may be carried out. The conditions of this optional second solvent extraction step are preferably similar to the first solvent extraction step. For example these two optional steps are performed by contacting the vegetable material with 85% ethanol in water at 80° C., during 2.5 hours at atmospheric pressure.

The vegetable material which is insoluble in the solvent is preferably separated from the solvent, for example by filtration and/or centrifugation. This solid material is subsequently used as the source of the polysaccharides in the aqueous water extraction step according to the method of the invention.

The extract obtained after the aqueous extraction contains the polysaccharides according to the invention. Also some solid material may be present in the extract, and this solid material can be separated from the extract by any suitable separation method, such as filtration or centrifugation. Optionally the solid residue is subsequently extracted again with water. Suitably the extraction conditions in this optional second step are the same as in the first aqueous extraction step.

Optionally the two or more aqueous extracts may be mixed to obtain a single extract containing the polysaccharide according to the invention. A dialysis step is optionally applied to the extract, in order to remove small molecules having a molecular weight below 10 kDa. The obtained extract after the first step is suitable to be used to modulate the immune system. Optionally coloured compounds may be removed by treatment of the extract with active coal, to absorb the coloured compounds.

In order to check the success of polysaccharide isolation, an overall content of carbohydrates can be determined using the Dubois method (Dubois, Analytical Chemistry, vol. 28, 1956, p. 350-356). A first rough insight in the success of removal of small oligosaccharides can be obtained by the average degree of polymerization (DP value) which is determined by comparing the analysis result on carbohydrate reducing end groups (DNSA method) with the total carbohydrate content determined by the Dubois method. Successful removal of small oligosaccharides (e.g. mono and disaccharides) would give a high average DP value (e.g. at least higher than 2). A more accurate way is to determine the molecular weight distribution of the enriched extract by size exclusion chromatography.

In the second step of the method according to the sixth aspect of the invention, the extracted polysaccharide according to the first aspect of the invention is purified. Preferably this separation involves two further purification steps: first a separation of acidic compounds in the extract from non-acidic compounds; and a second optional step to separate acidic compounds into fractions having different molecular weights, to obtain the polysaccharide according to the first aspect of the invention having a molecular weight of at least 70 kDa, preferably at least 110 kDa, preferably maximally 2,000 kDa.

In an optional first purification step first the acidic fraction is separated from non-acidic compounds. The polysaccharide according to the invention contains galacturonyl acid residues in the RG-I core, and these residues make the polysaccharide according to the invention acidic. The acidic fraction can be separated from the non-acidic fraction using ion exchange. The non-acidic fraction may for instance contain neutral polysaccharides such as starch. Subsequently the acidic fraction is separated into compounds having different molecular weights, for example by gel filtration. The cut-off value of the separation on molecular weight is at 70 kDa, meaning that only molecules having a molecular weight of at least 70 kDa are retained. Preferably the cut-off is at a molecular weight of at least 110 kDa, preferably with a maximum of 2,000 kDa. The resulting material is the polysaccharide according to the first aspect of the invention. Also fractions can be made, for example a fraction of compounds having a molecular weight between 70 and 110 kDa, and more than 110 kDa. The conditions required for ion exchange and gel filtration are known to the skilled person.

Preferably for ion exchange anion exchange materials are used as stationary phase like strong acidic resins e.g. Amberlite, Dowex and Mitshubishi (DIAION), either as gels or as beads or alternatively weak acidic ion exchanger like DEAE-sepharose or WK10/WK40 of DIAION, also as beads or gels. By application of a pH, buffer (Tris, Phosphate) or salt (NaCl) concentration gradient the acidic pectin is separated from the neutral polysaccharides. Suitably, first a neutral fraction is washed off and the subsequent acidic fraction is collected, concentrated and desalted e.g. by ultrafiltration over a 10 kDa membrane or dialysis prior to GPC. Preferably the gel filtration uses size exclusion materials as stationary phase e.g. Sephacryl 100-HR & 200-HR, Sephadex G-100, Superdex200. Suitably the sample is isocratically eluted in a buffer of strength between 0.01 to 0.2 M. The size exclusion column can be calibrated by $M_W$ standards using proteins or polysaccharides. A set of dextrans is preferred to use for this.

The total amount of polysaccharides in the extracts can be determined by any analytical technique known to the skilled person. For both ion exchange and gel filtration the preferred detection method is by monitoring UV absorbance between 210 and 220 nm as the carboxylate groups of the compounds show absorbance in this spectral region. Other detection methods could be by Refractive index (RI), Pulse Amperometic Detection (PAD), mass spectroscopy or off line analysis of the fractions by specific saccharide detecting reactions as the sulphuric acid/phenolic method as described by Dubois.

Finally the obtained, purified extract can be dried using any suitable method, such as freeze drying or spray drying.

A preferred method to obtain the polysaccharides according to the invention is as follows. A sample of a dried or fresh vegetable material is washed twice with 85% ethanol in water for 2.5 hours at 80° C. and once with 85% ethanol in water for 1.5 hours at 80° C. After decanting the ethanol, the pellets are dried. The polysaccharides are extracted from the pellet by adding demineralised water and boiling (at about 100° C. at atmospheric pressure) for 3 hours. After separation of dispersed material from the aqueous phase, e.g. by centrifugation, a pellet is resuspended in demineralised water and boiled again for 3 hours. The supernatants of the first and second extractions are collected, freeze dried and stored at room temperature.

In a preferred subsequent step, the polysaccharide enriched freeze dried extracts are suspended at a concentration of 2% (w/w) in phosphate buffered saline (PBS) is made and filtered clear and sterile through a 0.2 micrometer filter. As the polysaccharides according to the invention are soluble in water, the filtrates contain the polysaccharide according to the invention.

Preferably, effective separation is by using the weak ion exchange stationary phase DEAE-sepharose using a pH 7.5 Tris-HCl buffer and applying a salt gradient. The acidic fraction is desalted by ultrafiltration over a 10 kDa membrane prior to GPC and lyophilized. Subsequently the fraction is redissolved in volatile buffer (e.g. 0.1 M ammonium carbonate) and applied molecular weight distribution by size exclusion chromatography on Superdex 200 using a 5 ml/min flow. Detection by UV 214 nm absorbance and the Superdex column calibrated by dextran $M_W$ standards.

The most preferred option for some crops like carrots and apple is to skip the first column chromatography procedure and do only the size exclusion chromatography (molecular weight distribution) by gel filtration. The polysaccharide enriched extract is dissolved in volatile buffer (e.g. 0.1 M ammonium carbonate) and applied molecular weight distribution by size exclusion chromatography on Superdex 200 using a 5 ml/min flow. Detection by UV 214 nm absorbance and the Superdex column calibrated by dextran MW standards.

As the nature of the raw material from which the polysaccharides according to the invention varies, the conditions at which the optional extraction steps may be performed may vary as well. For example the amounts of solvent and water per gram of a given starting material may be different for various sources. These modifications are within the scope of the skilled person.

Preparation of the Polysaccharide

Apart from applying the extraction process from natural vegetable materials, the polysaccharides according to the invention may also be prepared by chemical and/or biotechnological processes. De novo synthesis starting from simple monosaccharides by usual synthetic chemical transformations is possible in principle, including enzymatic conversions. Alternatively from materials from natural sources which can be converted via usual chemical, including enzymatic, manipulations. Also via biomolecular techniques in which the polysaccharides are synthesized by a recombinant organism (like bacteria, fungi) in which the polysaccharide synthesizing cellular parts are expressed and activated to express the target polysaccharides stated in this patent.

Biotechnological production may involve plant cell cultures or callus cultures. Plant cell cultures inherently contain the rhamnosyltransferase and galacturonic acid transferase needed for the polysaccharide production, as well as the machinery to produce the activated monosaccharide donors for the transferases (e.g. UDP-rhamnose and UDP-galacturonic acid).

Production may also be achieved by biotechnological processes using microalgae, which represent monocellular primitive plants. Microalgal biotechnology has evolved rapidly during the last decade (Walker et al., 2005, Plant Cell Rep., vol. 24, p. 629-41), and genetic engineering of these species allows production of various products for both food and pharmaceutical use. Rhamnogalacturonan is not a typical microalgae polysaccharide, and thus the cells have to be transformed to express the key enzymes, rhamnosyltransferase and galacturonic acid transferase.

Yeast and fungi are established production hosts for numerous biotechnological products, and rhamnogalacturonan may well be produced by these hosts. Beside the polysaccharide building enzymes, the monosaccharide donor production machinery must be transferred to the cells.

Pure chemical synthesis of high-MW rhamnogalacturonan has not been described thus far. However, a RG-1 tetrasaccharide building block has been synthesized, and the chemistry developed allows chain elongation to larger structures (Rich et al., 1999, Tetrahedron: Asymmetry, vol. 10, p. 17-20).

Concentration of extract in microgram per milliliter (x-axis) versus percentage phagocytosis (y-axis).

Figure 3:
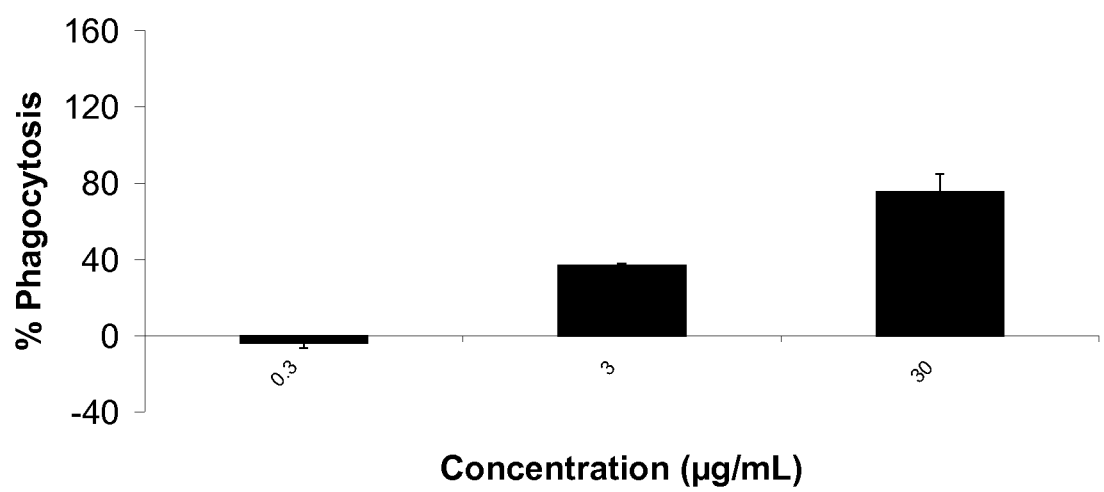

FIG. 3: Immune modulating effect of polysaccharides, obtained from the bean of the species *Glycine max* (soyabean); HL60 cell assay.

Concentration of extract in microgram per milliliter (x-axis) versus percentage phagocytosis (y-axis).

EXAMPLES

The following non-limiting examples illustrate the present invention.

Methods

Separation of Polysaccharides by Molecular Weight

Polysaccharides obtained by boiling water extraction are separated by gel filtration chromatography on a column of Superdex 200 (1×30 cm; GE Healthcare). The polysaccharide samples are dissolved in 0.1 M ammonium bicarbonate and aliquots of 5-15 mg were run on the column in the same buffer. Eluting components are detected by absorption at 214 nm.

The polysaccharides are pooled into three fractions: $M_W$>110 kDa, 70-110 kDa and 40-70 kDa. The pooling limits are determined by comparing to elution positions of Dextran standards 40 kDa, 70 kDa and 110 kDa (ex GE Healthcare).

Substitution and Composition Analysis of Polysaccharides

The composition of polysaccharide fractions as obtained from the extraction process are determined using NMR analysis. Prior to NMR analysis, dry polysaccharide samples (1-10 mg) are dissolved in deuterium oxide ($D_2O$) and dried in a vacuum centrifuge. Samples are then dissolved in 600 microliter of $D_2O$. Spectra are collected on a Varian Unity 500 NMR spectrometer at 296 K and referenced to internal acetone standard (2.225 ppm).

Referring to table 1, the polysaccharide substitution level and the molar composition of the building units are analysed by using the NMR data as follows:

Rhamnogalacturonan substitution level

The ratio of 4-substituted rhamnosyl units and nonsubstituted units is estimated by integrating the splitted rhamnose —$CH_3$ signals. The —$CH_3$ protons in 4-substituted rhamnosyl units resonate around 1.32 ppm, while those of the non-substituted rhamnosyl units at 1.25 ppm.

Molar ratio of galactans and arabinans

The molar amount of galactans and arabinans is analysed by integrating the observed β1,4-galactan H-1 signal (4.64 ppm) and the arabinan H-1 signals (-5Ara H-1, 5.09 ppm; -3,5Ara H-1 5.12 ppm; terminal Araα1-3 5.15 ppm; terminal Araα1-2 5.18 ppm; -2,3,5Ara H-1 5.26 ppm. These integration values are compared to the integrated rhamnose —$CH_3$ signals.

Polygalacturonic Acid/RG-I Ratio

The ratio of polygalacturonic acid to RG-I is analysed as follows: The total amount of galacturonic acid H-4 signals is integrated between 4.42 and 4.47 ppm, and the amount of rhamnose is obtained by integration of the —$CH_3$ signals (1.25-1.32 ppm). The H-4 signal of the RG-I specific GalAα1-2 unit is located in the same 4.42-4.47 signal, and its portion has to be deducted from the total H-4 signal. This value is the same as rhamnose amount, as RG-I is a 1:1 polymer of Rha and GalA. The remaining H-4 signal represents the share of polygalacturonic acid type GalAα1-4 H-4 signal.

In Vitro Assays

Two assays are used to determine the immunomodulating response of the polysaccharides in vitro, both based on phagocytosis activity. These assays are:

Whole Blood Cell Assay

Phagocytosis activity in whole blood is evaluated using the Phagotest® kit of Orpegen Pharma (Heidelberg, Germany) using an adjusted protocol. Fresh blood is obtained from healthy human volunteers in sodium heparin vacutainers (BD Biosciences). 30 microliter of whole blood and 5 microliter of the ingredient are incubated in duplicates for 30 minutes in a polypropylene 96-well plate at 37° C. in a water bath. Control incubations consisted of PBS (=basal phagocytosis activity) or 100 ng/mL *E. coli*-lipopolysaccharide (LPS) (=positive control sample) in triplicate measurements. After the incubation step, 10 microliter of FITC-labeled *E. coli* (white blood cell to *E. coli* ratio of 25:1) is added. This incubation at 37° C. is stopped after 6.5 minutes by adding 50 microliter of ice-cold quencher solution. The cells are washed three times by adding 230 microliter of ice-cold wash-buffer and centrifugation for 3 min at 300 g (4° C.). The erythrocytes are lysed using 290 microliter of lysis buffer. After incubation in the dark for 20 minutes at room temperature, the cells are centrifuged for 5 min at 300 g (4° C.). Cells are resuspended in 150 microliter of wash-buffer and stained with propidium iodide. Analysis is performed by flow cytometry (Coulter FC500 MPL flow cytometer, Beckman Coulter Nederland BV, Mijdrecht). Within the leucocytes, granulocytes are gated according to the FSC/SSC profile. The percentage of phagocytosing cells in the granulocyte population is determined. The results are normalized to the dynamic range between basal and LPS-stimulated phagocytosis and expressed as a relative percentage phagocytosis activity. A normalized percentage of more than 40% is considered to be positive.

HL60 Cell Assay

The human promyelocytic leukaemia cell line HL60 is used to determine the phagocytosis-enhancing capacity of the ingredients. This cell line can be differentiated towards the monocyte lineage with vitamin D3 and the cells subsequently obtain phagocytic capacity. 48 hours before the start of the assay, the HL60 cells are differentiated along the monocytic lineage by the addition of 1α,25-dihydroxyvitamin D3 (VitD3) to the medium. Upon differentiation, 200 microliter of HL60 cells ($8 \times 10^5$ cells/ml) are transferred to 96-wells flat-bottom plates in triplicates. Fluorescent labeled microspheres (ratio beads:cells, 19:1) are added and incubated for 24 hrs at 37° C. Control incubations consist of differentiated HL60 cells in PBS (=basal phagocytosis level) or 100 ng/mL *E. coli*-lipopolysaccharide (LPS) (=positive control sample) in triplicate measurements. After the incubation period, the cells are transferred to a 96-wells V-bottom plate, washed three times and fixed with formaldehyde. For analysis, the cells are transferred to a 96-wells clear-bottom plate and fluorescence intensity is analyzed using a Flex Station II fluorometer. The data are normalized using the positive control and expressed as a relative percentage phagocytosis activity. A normalized percentage of more than 40% is considered to be positive.

Example 1

Isolation and Characterisation of Polysaccharides

Various plant materials were used to extract polysaccharides. Polysaccharides were obtained from the following raw materials:

leaves of the species *Camellia sinensis* (tea); the composition of polysaccharides from several samples was determined;

roots of the species *Daucus carota* subsp. *sativus* (carrot);

fruit of the species *Malus domestica* (apple);

root of the species *Beta vulgaris* L. (sugar beet);

bean of the species *Glycine max* (soyabean), source of the polysaccharides is water-soluble soya polysaccharides ex Fuji Oil (Japan).

The procedure to obtain the materials was as follows. 25 g of methanol insoluble plant material was washed 2 times with 200 ml of 85% ethanol (VWR Prolabo) in water for 2.5 hours at 80° C. and 1 time with 200 ml of 85% ethanol in water for 1.5 hours at 80° C. After decanting the ethanol, the pellet was dried overnight in a fuming cabinet. The polysaccharides were extracted by adding 200 ml of demineralised (MilliQ) water and boiling for 3 hours at atmospheric pressure. After centrifugation at 2,000 g for 20 min at room temperature (RT), the pellet was re-suspended in 200 ml of demineralised (MilliQ) water and boiled again for 3 hours. The supernatants of the first and second extraction were collected, freeze dried and stored at room temperature.

From the polysaccharide enriched freeze dried extracts a 2% (w/w) suspension in demineralised water was made and autoclaved at a temperature of about 121° C. during about 15 minutes. The suspension was centrifuged at 2,000 g for 30 minutes at room temperature. The supernatants were further purified by filtering through a 0.2 micrometer filter, divided in small portions and stored at −20° C.

Subsequently, about 650 mg of extract was dissolved in 30 ml of 20 mM Tris-HCl, pH 7.5, and allowed to dissolve with frequent mixing for 1 hour. Insoluble matter was removed by centrifugation and the clear supernatant was subjected to anion-exchange chromatography on a column of DEAE-sepharose (50×150 mm, ca. 290 ml) equilibrated with 20 mM Tris-HCl, pH 7.5, at a flow rate of 10 ml/min. After injection, the column was run isocratically with the equilibration buffer for 30 min, followed by a gradient of 0-1 M NaCl over 30 min, and 1 M NaCl for additional 40 min. Absorbance at 214 nm was recorded and fractions of 25 ml collected. The acid fraction was concentrated and desalted by ultrafiltration over a 10 kDa membrane prior to GPC. The yield was not measured at this point.

The acid fractions obtained above were combined (from multiple runs) and then subjected to gel-filtration chromatography on a column of Superdex 200 (5 cm diameter, 95 cm length). Superloop was used in the injection due to large sample volumes. The column was eluted at a flow rate of 5 ml/min with 100 mM ammonium bicarbonate and the absorbance at 214 nm was recorded. Fractions of 25 ml were collected.

Polysaccharides from apple were obtained in the following way. Fresh apples were grated and treated with an experimental pectolytic enzyme preparation, Rapidase C600 (0.02% w/w, 4 h at 45° C.; enzyme obtained from Gist Brocades, Delft, the Netherlands). The soluble part was recovered by centrifugation, and subjected to ultrafiltration on a 60 kDa molecular weight cut-off membrane, and then lyophilized. This fraction was further saponified to remove labile methyl and acetyl esters: a sample of 50.4 mg of apple RG was dissolved in 5 ml of 0.2 M sodium carbonate, pH 10, and allowed to react for 18 h at room temperature. The reaction mixture was then dialyzed for 24 h with three solution changes against 50 mM ammonium bicarbonate in MWCO 6000-8000 dialysis tubing. Finally, the sample was subjected to SPE in C-18 silica.

The following compositions of polysaccharides obtained from various sources were determined.

TABLE 1

Substitution and composition analysis of polysaccharides obtained from various sources; polysaccharide fractions separated on Superdex 200.

| Material and $M_W$ fraction | Rha 4-OH subst. [1] | β1-4Gal [2] | Ara [3] | α1-4GalA [4] |
|---|---|---|---|---|
| Tea #7 | | | | |
| >110 kDa | 45% | 3 | 5 | — [5] |
| 70-110 kDa | 45% | 2 | 3 | — [5] |
| 40-70 kDa (comparative as $M_W$<70) | 65% | 3 | 3 | — [5] |
| Tea #15 | | | | |
| >110 kDa | 50% | 6.5 | 0.5 | — [5] |
| 70-110 kDa | 70% | 8 | 1.5 | — [5] |
| 40-70 kDa (comparative as $M_W$<70 kDa) | 60% | 9 | 0.8 | — [5] |
| Tea #218 | | | | |
| >110 kDa | 35% | 17 | 19 | — [5] |
| 70-110 kDa (comparative as GalA:Rha >2.5) | 70% | 8 | 20 | 46 |
| Tea #244 | | | | |
| >110 kDa | 37.50% | 7.5 | 11 | — [5] |
| 70-110 kDa (comparative as GalA:Rha >2.5) | 50% | 3 | — | 55 |
| Apple | | | | |
| >110 kDa | 80% | 3 | 3 | — [5] |
| 70-110 kDa | 60% | 1.5 | 1 | 1.2 |
| 40-70 kDa (comparative as $M_W$<70 kDa) | 80% | 2 | 0.7 | 1.5 |
| Sugar beet | | | | |
| >110 kDa | 60% | 1.7 | 29 | — [5] |
| 70-110 kDa | 60% | 1.9 | 20 | — [5] |
| 40-70 kDa (comparative as $M_W$<70 kDa) | 45% | 2.1 | 11 | — [5] |
| Carrot | | | | |
| >110 kDa | 55% | 15 | 17 | — [5] |
| 70-110 kDa (comparative as GalA:Rha >2.5) | 70% | 5 | 10 | 16 |
| 40-70 kDa (comparative as $M_W$<70 kDa) | 40% | 1.5 | 6 | 16 |

TABLE 1-continued

Substitution and composition analysis of polysaccharides obtained from various sources; polysaccharide fractions separated on Superdex 200.

| Material and $M_W$ fraction | Rha 4-OH subst. [1] | β1-4Gal [2] | Ara [3] | α1-4GalA [4] |
|---|---|---|---|---|
| Soya | | | | |
| >110 kDa | 55% | 44 | 23 | — |
| 70-110 kDa | 50% | 26 | 13 | — |
| 40-70 kDa (comparative as $M_W$ <70 kDa) | 40% | 6 | 4 | 3 |

Legend:
[1] Rha 4-OH subst.: molar fraction of the Rha moieties in the RG-I core which is substituted at the C-4 position with a side chain; as measured from the Rha CH$_3$ signal shift;
[2] β1-4Gal: molar ratio of beta(1,4)-linked Gal as compared to Rha (mol/mol); relates to the length of side chains containing beta(1,4)-linked galactan residues;
[3] Ara: molar ratio of alpha(1,5)-linked arabinan as compared to Rha (mol/mol); relates to the length of side chains containing alpha(1,5)-linked arabinosyl residues;
[4] α1-4GalA: alpha-1,4-galacturonyl acid residues vs. rhamnosyl residues (mol/mol); i.e. this number indicates the molar ratio between GalA residues in the alpha(1,4)-linked polygalacturonic acid or alpha(1,4)-linked oligogalacturonic acid cores in the polysaccharide and Rha residues in the RG-I core of the polysaccharide;
[5] Below measurable level; i.e. the amount of alpha(1,4)-linked GalA residues present in the polysaccharide originating from the alpha(1,4)-linked polygalacturonic acid or alpha(1,4)-linked oligogalacturonic acid cores is so low that it is not detectable. If this is the case, then the ratio GalA:Rha is 1.

Example 2

Immunomodulating Effect of Polysaccharides from Various Sources

The immuno-modulating effect of various samples have been determined at various concentrations, using the two assays as described above. The results are given in the following table.

Polysaccharides were obtained from the following raw materials:

leaves of the species *Camellia sinensis* (tea); the immuno modulating effect of a pooled mix of samples of tea #7, tea #15, tea #218, tea #244 (see table 1) is indicated in the table below;

roots of the species *Daucus carota* subsp. *sativus* (carrot);

fruit of the species *Malus domestica* (apple);

root of the species *Beta vulgaris* L. (sugar beet);

bean of the species *Glycine max* (soyabean).

TABLE 2

In vitro immune modulating activity of various samples, tested using whole blood cell assay, and/or HL60 cell assay. Concentration of extract (microgram per milliliter) obtained according to method above, versus phagocytosis activity of assay.

| | whole blood cell assay | | HL60 cell assay | |
|---|---|---|---|---|
| Material and $M_W$ fraction | 3 microgram/ml | 30 microgram/ml | 0.3 microgram/ml | 3 microgram/ml |
| Tea | | | | |
| >110 kDa | + | ++ | + | ++ |
| 70-110 kDa | − | ++ | − | + |
| Apple | | | | |
| >110 kDa | ++ | ++ | ++ | ++ |
| 70-110 kDa | − | ++ | − | + |
| 40-70 kDa (comparative as $M_W$ <70 kDa) | | | | |

TABLE 2-continued

In vitro immune modulating activity of various samples, tested using whole blood cell assay, and/or HL60 cell assay. Concentration of extract (microgram per milliliter) obtained according to method above, versus phagocytosis activity of assay.

| | whole blood cell assay | | HL60 cell assay | |
|---|---|---|---|---|
| Material and $M_W$ fraction | 3 microgram/ml | 30 microgram/ml | 0.3 microgram/ml | 3 microgram/ml |
| Sugar beet | | | | |
| >110 kDa | + | ++ | | |
| Carrot | | | | |
| >110 kDa | ++ | ++ | − | ++ |

Figure 1:
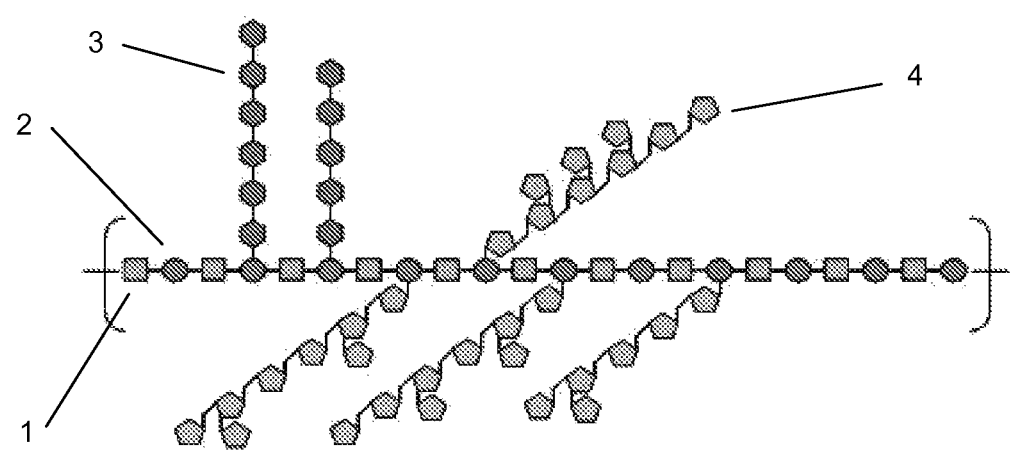
FIG. 1: Schematic representation of a preferred polysaccharide according to the invention:
1: galacturonyl acid residue in RG-I core
2: rhamnosyl residue in RG-I core
3: galactosyl residue in side chain, connected to 4-OH position of the rhamnosyl residue
4: arabinosyl residue in side chain, connected to 4-OH position of the rhamnosyl residue
Figure 2:
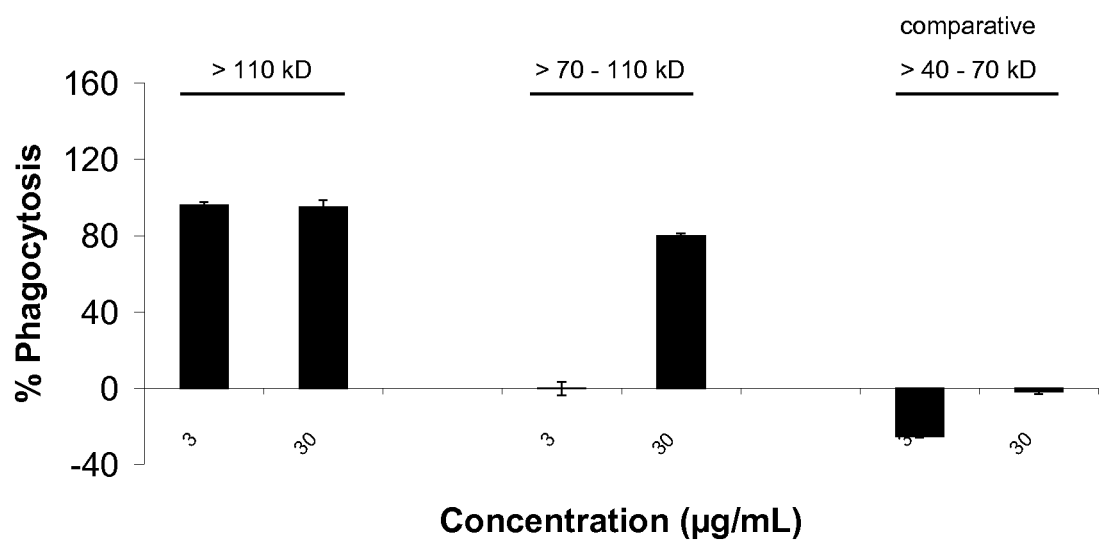
FIG. 2: Immune modulating effect of polysaccharides, obtained from the fruit of the species *Malus domestica* (apple); whole blood cell assay.

Legend:
++ very positive effect (% phagocytosis >80%)
+ positive effect (% phagocytosis 40%-80%)
− no effect
blank: not tested FIGS. 2 and 3 indicate the measured phagocytosis percentage, for some of the polysaccharide samples:

FIG. 2: Apple (as in table 1 and 2), whole blood cell assay.

FIG. 3: Soyabean; HL60 cell assay; this sample not in table 2, soyabean polysaccharides: Rhamnogalacturonan (Soy Bean) ex Megazyme International Ireland Ltd. (Wicklow, Ireland).

Two of the samples obtained from the tea plant (*Camellia sinensis*) were also tested in the two tests, at lower concentrations this time. These samples were tea #7 and tea #15. Also the samples from carrot and apple were tested. The structural features of these materials have already been given in table 1. The results of these tests are the following:

TABLE 3

In vitro immune modulating activity of two samples obtained from the plant *Camellia sinensis*, and from carrot and apple, tested using whole blood cell assay, and/or HL60 cell assay. Concentration of extract (microgram per milliliter) obtained according to method above, versus phagocytosis activity of assay.

| Material and $M_W$ fraction | whole blood cell assay | | HL60 cell assay | |
|---|---|---|---|---|
| | 0.03 microgram/ml | 0.3 microgram/ml | 0.003 microgram/ml | 0.03 microgram/ml |
| Tea #7 | | | | |
| >110 kDa | ++ | ++ | | |
| 70-110 kDa | ++ | ++ | | |
| 40-70 kDa | − | ++ | | |
| Tea #15 | | | | |
| >110 kDa | ++ | ++ | ++ | ++ |
| 70-110 kDa | ++ | ++ | − | − |
| 40-70 kDa | − | ++ | − | − |
| Carrot | | | | |
| >110 kDa | − | − | | |
| 70-110 kDa | − | − | | |
| 40-70 kDa | − | − | | |
| Apple | | | | |
| >110 kDa | − | − | | |
| 70-110 kDa | − | − | | |
| 40-70 kDa | − | − | | |

Legend:
++ very positive effect (% phagocytosis >80%)
+ positive effect (% phagocytosis 40%-80%)
− no effect
blank: not tested This example shows that the extracts obtained from the plant *Camellia sinensis* showed very high immunostimulating activity in vitro. Already at concentrations as low as 0.003 microgram per milliliter, already a very high immunostimulating activity was measured in the whole blood cell assay, as compared to various other polysaccharides obtained from other vegetable materials. Polysaccharides obtained from apple or from carrot did not show immunostimulating effect in the whole blood cell assay at concentrations of 0.03 and 0.3 microgram per milliliter.

Example 3

Properties of Polysaccharide

During the isolation of polysaccharides from carrot, it was observed that these polysaccharides did not lead to thickening of fluids in which it was dissolved. This is in contrast to normal pectins, wherein similar concentrations of polymer lead to thickening of the fluids.

The invention claimed is:

1. A method of stimulating immune response in a mammal, comprising administering to a mammal in need of stimulation of its immune responsiveness a composition, wherein:
   (a) the composition comprises 0.5 to 25 wt. % of the polysaccharide;
   (b) the polysaccharide has a molecular weight of at least 110 kDa;
   (c) 20-90 mol. % of the rhamnosyl residues in the backbone of the polysaccharide are substituted at the 4-OH position;
   (d) the backbone of the polysaccharide comprises one or more side chains comprising alpha(1,5)-linked arabinosyl residues, said side chains being substituted at the 4-OH position of the rhamnosyl residue, and the molar ratio of arabinosyl residues to rhamnosyl residues being between 50:1 and 1:2;
   (e) the backbone of the polysaccharide comprises one or more side chains comprising beta(1,4)-linked galactosyl residues, said side chains being substituted at the 4-OH position of the rhamnosyl residue, and the molar ratio of galactosyl residues to rhamnosyl residues being between 50:1 and 1:1;
   (f) the backbone comprising alternating rhamnogalacturonan-I cores and alpha(1,4)-linked polygalacturonic acid or alpha(1,4)-linked oligogalacturonic acid cores, wherein the molar ratio of galacturonyl acid residues to rhamnosyl residues in the backbone of the polysaccharide ranges from 2.5:1 to 1:1;
   (g) less than 2 mol. % of galactosyl residues present in the side chains are beta(1,3)-linked or beta(1,6)-linked galactosyl residues; and
   (h) the polysaccharide is administered at a daily dose of at least 10 mg.

2. The method according to claim 1, for treating common cold.

3. The method according to claim 1, wherein the polysaccharide is administered as an adjuvant for a vaccine.

4. The method according to claim 1, wherein the polysaccharide has a molecular weight between 110 and 2,000 kDa.

5. The method according to claim 1, wherein the rhamnogalacturonan-I core comprises:
   (a) one or more side chains comprising a backbone of at least one or more alpha(1,5)-linked arabinosyl residues and wherein the one or more side chains are substituted at the 4-OH position of the rhamnosyl residues, wherein the polysaccharide has a molar ratio of arabinosyl residues to rhamnosyl residues between 50:1 and 1:2, and
   (b) the one or more side chains comprising a backbone of at least one or more beta(1,4)-linked galactosyl residues and wherein the one or more side chains are substituted at the 4-OH position of the rhamnosyl residues, wherein the polysaccharide has a molar ratio of galactosyl residues to rhamnosyl residues between 50:1 and 1:1.

6. The method according to claim 1, wherein the composition comprises 3 to 25 wt. % of the polysaccharide.

* * * * *